United States Patent
Mayya et al.

(10) Patent No.: US 12,303,207 B2
(45) Date of Patent: May 20, 2025

(54) AUTOMATED PLANNING OF SHOULDER STABILITY ENHANCEMENT SURGERIES

(71) Applicant: HOWMEDICA OSTEONICS CORP., Mahwah, NJ (US)

(72) Inventors: Maximilien Mayya, Antibes (FR); Jean Chaoui, Locmaria Plouzané (FR)

(73) Assignee: Howmedica Osteonics Corp., Mahwah, NJ (US)

(*) Notice: Subject to any disclaimer, the term of this patent is extended or adjusted under 35 U.S.C. 154(b) by 763 days.

(21) Appl. No.: 17/607,323

(22) PCT Filed: May 8, 2020

(86) PCT No.: PCT/US2020/032085
§ 371 (c)(1),
(2) Date: Oct. 28, 2021

(87) PCT Pub. No.: WO2020/236441
PCT Pub. Date: Nov. 26, 2020

(65) Prior Publication Data
US 2022/0202496 A1    Jun. 30, 2022

Related U.S. Application Data

(60) Provisional application No. 62/850,238, filed on May 20, 2019.

(51) Int. Cl.
*A61B 34/10* (2016.01)
*A61B 34/00* (2016.01)
*A61F 2/30* (2006.01)

(52) U.S. Cl.
CPC .............. *A61B 34/10* (2016.02); *A61B 34/25* (2016.02); *A61B 2034/104* (2016.02); *A61B 2034/105* (2016.02); *A61F 2/30942* (2013.01)

(58) Field of Classification Search
CPC ........ A61B 2034/104; A61B 2034/105; A61B 34/10; A61B 34/25; A61F 2/30942
See application file for complete search history.

(56) References Cited

U.S. PATENT DOCUMENTS 10,806,517 B2 * 10/2020 Bonny ................. A61B 17/154
11,020,128 B2 *  6/2021 Guilloux ............ A61B 17/1684
(Continued)

FOREIGN PATENT DOCUMENTS

CN      106999245 A     8/2017
CN      107924709 A     4/2018
(Continued)

OTHER PUBLICATIONS

David Saliken et al., "Imaging methods for quantifying glenoid and Hill-Sachs bone loss in traumatic instability of the shoulder: a scoping review," Jul. 18, 2015, BMC Musculoskeletal Disorders (2015) 16:164, pp. 1-22.*

(Continued)

*Primary Examiner* — Omar S Ismail
(74) *Attorney, Agent, or Firm* — Shumaker & Sieffert, P.A.

(57) ABSTRACT

Techniques and systems are described for planning shoulder stability enhancement surgeries. A computing system may determine a size of a predicted premorbid glenoid bone of the patient of a patient, a size of a Bankart lesion on a morbid glenoid bone of the patient, and a size of a geodesic surface on a 3-dimensional model of a predicted premorbid humerus of the patient. The geodesic surface is defined at least in part by a projected medial border of a Hill-Sachs lesion on a morbid humerus and a projected medial border of a footprint of a humeral head of the morbid humerus. The computing system may determine, based on the three areal sizes, whether bone loss of the patient involves joint engagement. The computing system may output an indication of whether (Continued)

a shoulder stability enhancement surgery that includes a bone graft is recommended for the patient.

20 Claims, 16 Drawing Sheets

(56) References Cited

U.S. PATENT DOCUMENTS

| | | | |
|---|---|---|---|
| 2008/0312663 A1 | 12/2008 | Haimerl et al. | |
| 2011/0304332 A1* | 12/2011 | Mahfouz | A61F 2/30942 |
| | | | 324/309 |
| 2013/0110470 A1* | 5/2013 | Vanasse | B29C 33/3835 |
| | | | 703/1 |
| 2014/0336539 A1* | 11/2014 | Torres | A61B 5/162 |
| | | | 600/595 |
| 2015/0073424 A1* | 3/2015 | Couture | A61B 17/1778 |
| | | | 606/96 |
| 2016/0256222 A1* | 9/2016 | Walch | A61F 2/4081 |
| 2016/0310285 A1 | 10/2016 | Kovacs et al. | |
| 2017/0105716 A1* | 4/2017 | Burkhart | A61B 17/0485 |
| 2017/0258390 A1* | 9/2017 | Howard | A61B 5/4803 |
| 2017/0360566 A1* | 12/2017 | Sikora | A61F 2/4657 |
| 2018/0008350 A1* | 1/2018 | Varadarajan | G16H 50/50 |
| 2018/0233222 A1 | 8/2018 | Daley et al. | |
| 2018/0280148 A1* | 10/2018 | Winslow | A61F 2/4612 |
| 2018/0325618 A1 | 11/2018 | Justin et al. | |
| 2020/0037942 A1* | 2/2020 | Howard | A61B 5/4088 |
| 2020/0060566 A1* | 2/2020 | Howard | A61B 5/4824 |
| 2021/0038315 A1* | 2/2021 | Bonny | A61F 2/389 |

FOREIGN PATENT DOCUMENTS

| | | | |
|---|---|---|---|
| JP | 2015511511 A | | 4/2015 |
| JP | 2018516634 A | | 6/2018 |
| RU | 2573803 C | | 8/2014 |
| RU | 2573803 C1 | * | 1/2016 |
| RU | 2017100873 A | | 1/2017 |
| WO | 2013062850 A1 | | 5/2013 |
| WO | 2018067966 A1 | | 4/2018 |
| WO | 2020205247 A1 | | 10/2020 |
| WO | 2020205248 A1 | | 10/2020 |

OTHER PUBLICATIONS

Eliji Itoi ,"'On-track' and off-track' shoulder lesions," Aug. 1, 2017, EOR|vol. 2,Aug. 2017, pp. 344-350.*
Dragomir Mijic et al.,"Computer-Assisted Planning and Patient-Specific Instrumentation (PSI) in Shoulder Arthroplasty," Feb. 10, 2019,Springer, Cham. https://doi.org/10.1007/978-3-030-02756-8_2 pp. 15-20.*
Eamon Ramhamadany et al. ,"Current concepts in the management of recurrent anterior gleno-humeral joint instability with bone loss,"Jun. 18, 2016,World J Orthop Jun. 18, 2016;vol. 7|Issue 6,pp. 343-350.*
Jack G. Skendzel et al.,"Diagnosis and Management of Humeral Head Bone Loss in Shoulder Instability," Feb. 17, 2012, The American Journal of Sports Medicine, vol. 40, No. 11,pp. 2633-2642.*
Hidetomo Saito et al.,"Location of the Hill-Sachs lesion in shoulders with recurrent anterior dislocation," Mar. 20, 2009, Arch Orthop Trauma Surg (2009) 129,pp. 1327-1333.*
Polydoor Emile Huijsmans et al., "Recurrent anterior shoulder instability: accuracy of estimations of glenoid bone loss with computed tomography is insufficient for therapeutic decision-making,"May 21, 2011,Skeletal Radio(2011)40,pp. 1329-1332.*
Nirav H.Amin et al.,"The Evaluation of Hill-Sachs Injuries and the Use of Humeral HeadAllograft for Repair of Hill-Sachs and Reverse Hill-Sachs Injuries," Mar. 2015,Operative Techniques in Sports Medicine,vol. 23, Issue 1,2015,pp. 11-15.*
Birgit S. Werner et al.,"The influence of three-dimensional planning on decision-making in total shoulder arthroplasty,"Aug. 2017,J Shoulder Elbow Surg (2017),vol. 26, Issue 8,pp. 1478-1481.*

G. Moineaua et al.,"Three-dimensional measurement method of arthritic glenoid cavity morphology: Feasibility and reproducibility," Jun. 22, 2012, Orthopaedics & Traumatology: Surgery & Research (2012) 98S,pp. S139-S143.*
Aysun Sezer et al.,"Segmentation of Bone with Region Based Active Contour Model in PD Weighted MR Images of Shoulder,"May 7, 2015,Computational and Mathematical Methods in Medicine,vol. 2015,pp. 1-11.*
First Examination Report from counterpart Australian Application No. 2020279597 dated Aug. 4, 2022, 2 pp.
Response to Communication Pursuant to Rules 161(1) and 162 EPC dated Jan. 5, 2022, from counterpart European Application No. 20729419.0, filed Jul. 5, 2022, 16 pp.
Office Action, and translation thereof, from counterpart Japanese Application No. 2021-569011 dated Sep. 13, 2023, 4 pp.
Notice of Intent to Grant and Text Intended to Grant from counterpart European Application No. 20729419.0 dated Jul. 13, 2023, 59 pp.
Notice of Acceptance for patent application from counterpart Australian Application No. 2020279597 dated Oct. 18, 2022, 9 pp.
Response to Communication pursuant to Article 94(3) EPC dated Nov. 18, 2022, from counterpart European Application No. 20729419.0 filed Mar. 2, 2023, 14 pp.
Response to First Examination Report dated Aug. 4, 2022, from counterpart Australian Application No. 2020279597 filed Sep. 23, 2022, 84 pp.
Notice of Intent to Grant and Text Intended to Grant from counterpart European Application No. 20729419.0 dated Nov. 27, 2023, 111 pp.
Notice of Intent to Grant from counterpart Japanese Application No. 2021-569011 dated Jan. 9, 2024, 5 pp.
Response to Communication Pursuant to Rules 71(3) EPC dated Jul. 13, 2023, from counterpart European Application No. 20729419.0, filed Nov. 13, 2023, 14 pp.
Response to Office Action dated Sep. 13, 2023, from counterpart Japanese Application No. 2021-569011 filed Nov. 27, 2023, 11 pp.
Extended Search Report from counterpart European Application No. 23218791.4 dated Apr. 2, 2024, 6 pp.
First Office Action and Search Report, and translation thereof, from counterpart Chinese Application No. 202080037784.9 dated Jan. 25, 2024, 10 pp.
Notice of Intent to Grant from counterpart Chinese Application No. 202080037784.9 dated May 31, 2024, 3 pp.
Communication pursuant to Article 94(3) EPC from counterpart European Application No. 20729419.0 dated Nov. 18, 2022, 4 pp.
Office Action, and translation thereof, from counterpart Japanese Application No. 2021-569011 dated Apr. 4, 2023, 11 pp.
"Blueprint 3d Planning Software + PSI," Wright Medical Group, retrieved from https://www.wright.com/blueprint-3d-planning-psi-system on Oct. 15, 2020, 9 pp.
"Hololens 2," Microsoft Hololens, retrieved from https://www.microsoft.com/en-us/hololens, on Oct. 15, 2020, 5 pp.
Balg et al., "The instability severity index score—A simple Pre-Operative score to select patients for arthroscopic or open shoulder stabilization," The Journal of Bone & Joint Surgery, vol. 89-B, No. 11, Nov. 2007, 8 pp.
Huijsmans et al., "Recurrent anterior shoulder instability: accuracy of estimations of glenoid bone loss with computed tomography is insufficient for therapeutic decision-making," Skeletal Radiology, vol. 40, No. 10, May 2011, 6 pp.
International Preliminary Report on Patentability from International Application No. PCT/US2020/032085, dated Dec. 2, 2021, 8 pp.
International Search Report and Written Opinion of International Application No. PCT/US2020/032085, dated Sep. 4, 2020, 13 pp.
Toi, E., "'On-track' and 'off-track' shoulder lesions," EFORT Open Reviews, vol. 2, No. 8, Aug. 2017, 9 pp.
Moineau et al., "Three-dimensional measurement method of arthritic glenoid cavity morphology: Feasibility and reproducibility," Orthopaedics & Traumatology: Surgery & Research, vol. 98, No. 6, Supplement, Sep. 2012, 7 pp.
Ozturk et al., "Management of a first episode of antero-inferior shoulder dislocation in an athlete," Revue Medicale Suisse, Sports Medicine, vol. 14, 613, Jul. 2018, 18 pp. with translation.

(56) References Cited

OTHER PUBLICATIONS

Ramhamadany et al., "Current concepts in the management of recurrent anterior gleno-humeral joint instability with bone loss," World Journal of Orthopedics, vol. 7, No. 6, Jun. 2016, 12 pp.

Saliken et al., "Imaging methods for quantifying glenoid and Hill-Sachs bone loss in traumatic instability of the shoulder: a scoping review," BMC Musculoskeletal Disorders, vol. 16, No. 164, Jul. 2015, 26 pp.

Shaha et al., "Clinical Validation of the Glenoid Track Concept in Anterior Glenohumeral Instability," The Journal of Bone and Joint Surgery, American vol. vol. 98-A, No. 22, Nov. 2016, 6 pp.

Surazhsky et al., "Fast exact and approximate geodesics on meshes," ACM Transactions on Graphics, vol. 24, No. 3, Jul. 2005, 8 pp.

Wright Medical, "BluePrint Video-Wright Medical Announces the Acquisition of IMASCAP SAS", accessed from www.imascap.com/wp-content/uploads/2017/12/blueprintvid.mp4, Dec. 14, 2017, 9 pp.

Wright, "BluePrint, 3d Planning + PSI," User Manual V2.1, Tomier, CAW-8754, Nov. 2017, 18 pp.

Response to Office Action, and translation thereof, dated Apr. 4, 2023, from counterpart Japanese Application No. 2021-569011 filed Jun. 13, 2023, 15 pp.

Response to Extended Search Report dated Apr. 2, 2024, from counterpart European Application No. 23218791.4 filed Oct. 25, 2024, 22 pp.

\* cited by examiner

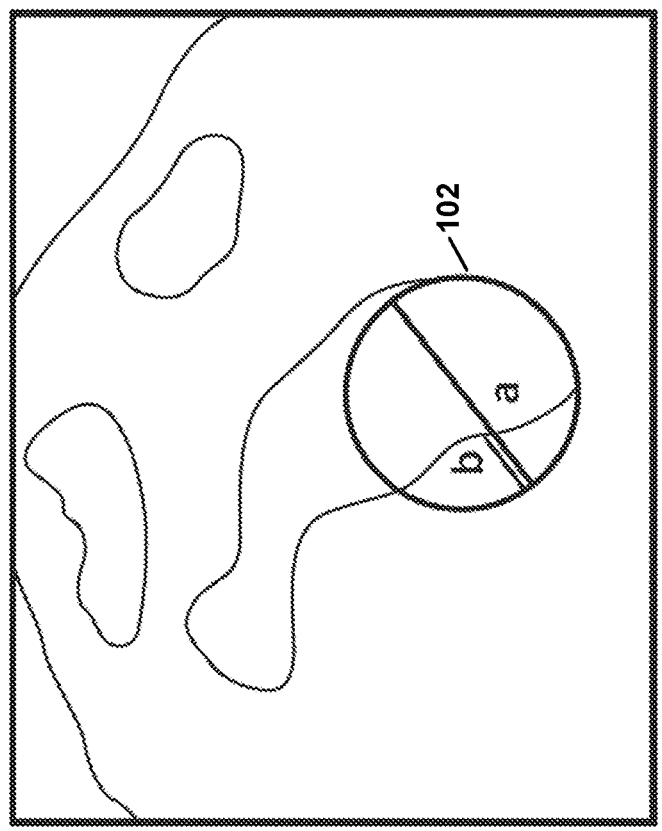
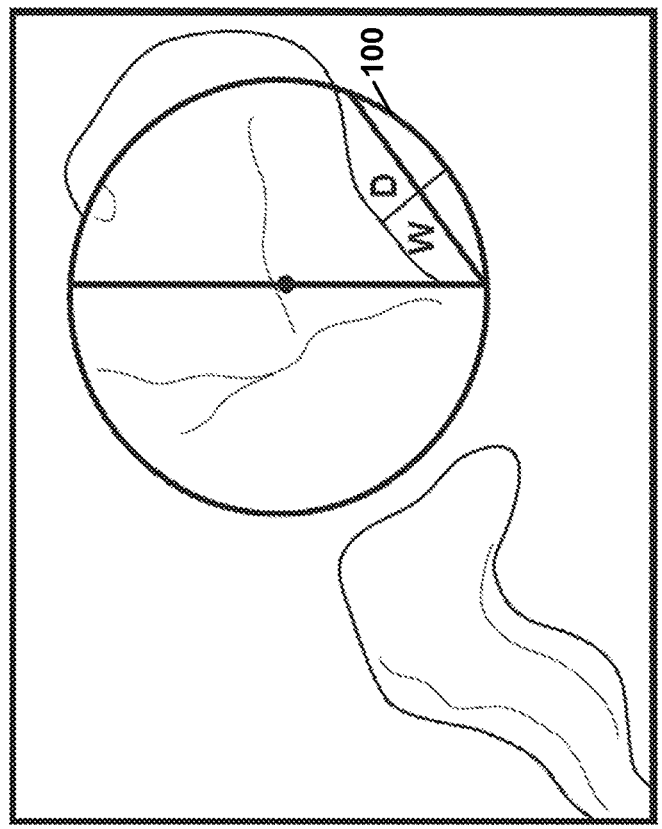
FIG. 1B
FIG. 1A

| Prognostic factors | Points |
| --- | --- |
| Age at surgery (yrs) | |
| ≤ 20 | 2 |
| > 20 | 0 |
| | |
| Degree of sport participation (pre-operative) | |
| Competitive | 2 |
| Recreational or none | 0 |
| | |
| Type of sport (pre-operative) | |
| Contact or forced overhead | 1 |
| Other | 0 |
| | |
| Shoulder hyperlaxity | |
| Shoulder hyperlaxity (anterior or inferior) | 1 |
| Normal laxity | 0 |
| | |
| **Hill-Sachs on AP* radiograph** | |
| Visible in external rotation | 2 |
| Not visible in external rotation | 0 |
| | |
| Glenoid loss of contour on AP radiograph | |
| Loss of contour | 2 |
| No lesion | 0 |
| | |
| Total (points) | 10 |

FIG. 5

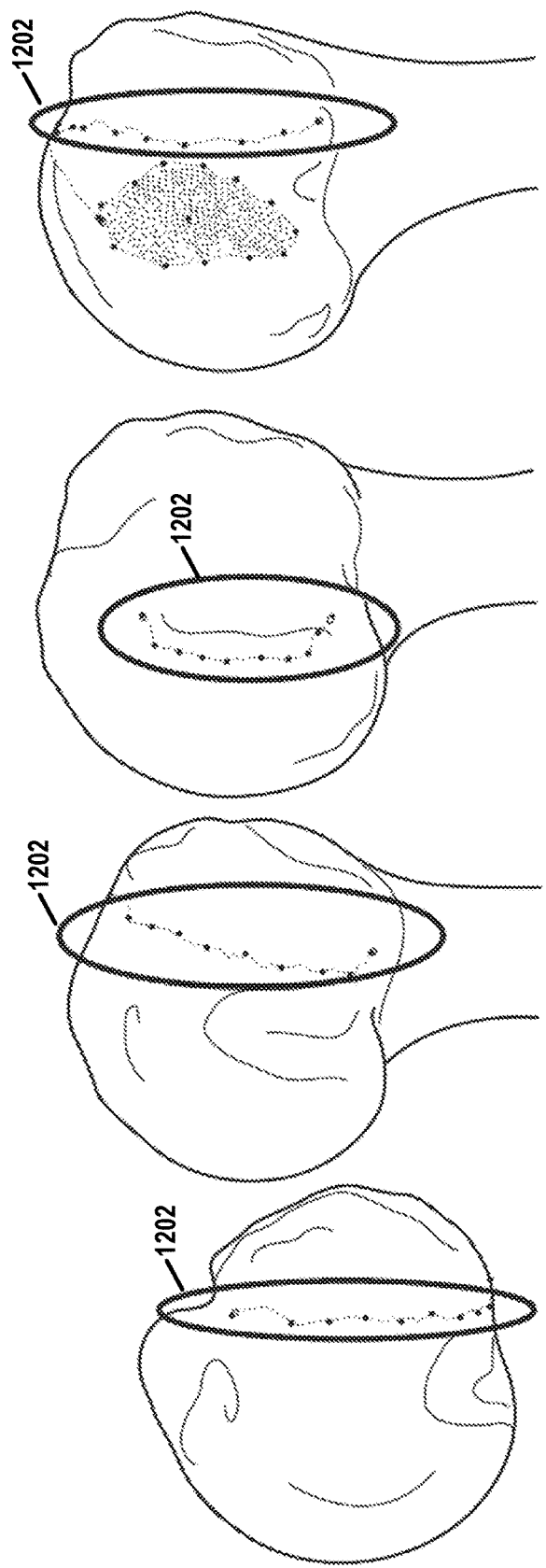

AUTOMATED PLANNING OF SHOULDER STABILITY ENHANCEMENT SURGERIES

This application is a national stage application under 35 U.S.C. § 371 of PCT Application No. PCT/US2020/032085, filed May 8, 2020, which claims the benefit of U.S. Provisional Application No. 62/850,238, filed May 20, 2019.

BACKGROUND

Shoulder instability refers to a variety of disorders that result in dislocation, subluxation (partial dislocation) or a general lack of stability of a patient's glenohumeral joint. Individuals may experience shoulder instability because of trauma or congenital laxity of shoulder structures, or because of weakness and improper biomechanics, such as poor movement patterns. Medical professionals typically classify shoulder instability according to the degree of extra movement in the glenohumeral joint, how often instability occurs in the glenohumeral joint, the tissues affected, and the direction in which the shoulder becomes unstable.

There are four types of shoulder instability: anterior, posterior, inferior or multidirectional. Anterior shoulder instability is the most common type, occurring in 95% of cases. Anterior shoulder instability is typically caused by trauma. Types of trauma that cause anterior shoulder instability frequently include combinations of excessive abduction, extension, and external rotation of the arm, which may occur during a skiing fall with the arm out to the side, during a clothesline tackle, or by blocking a spiked ball in volleyball.

There are currently four primary types of surgical procedures that may be used to handle cases of anterior shoulder instability: an arthroscopic Bankart surgery, a Hill-Sachs remplissage surgery, a Bristow surgery, and a Latarjet surgery. The Bristow surgery and the Latarjet surgery involve the harvesting of a bone graft from a tip of a coracoid process of a scapula of the patient and attaching the bone graft to a glenoid of the scapula. The bone graft subsequently helps to keep the humeral head of the patient in the glenoid cavity.

A surgeon may select from among these surgical procedures based on a diagnosis of a cause of the anterior shoulder instability. To decide which type of surgical procedure to use for an individual patient, the surgeon may calculate an Instability Severity Index Score (ISIS) for the patient. The surgeon may then use the ISIS for the patient, along with other information, to determine a path to follow in a decision tree. Other decisions in the decision tree rely on anatomic factors based on 2-dimensional or 3-dimensional computed tomography (CT) or Magnetic Resonance Imaging (MM) scans.

SUMMARY

This disclosure describes example systems and techniques for automated planning of shoulder stability enhancement surgeries. Current processes for planning shoulder stability enhancement surgeries may be laborious for surgeons and may be prone to errors. Such errors may cause surgeons to arrive at incorrect conclusions about the types of surgery to perform. For example, current processes may require the surgeon to manually determine amounts of bone loss and manually determine whether a Hill-Sachs lesion on a humeral head engages the glenoid bone during abduction and external rotation of the glenohumeral joint. These determinations are subject to human error and may be dependent on correct orientation of a patient during 2-dimensional imaging and/or correct positioning of a 3-dimensional model.

The techniques of this disclosure may improve reliability and accuracy of certain aspects of the planning process for shoulder stability enhancement surgeries. For example, as described herein, a computing system may use 3-dimensional models to determine whether bone loss of a patient involves joint engagement and, based on this, output an indication of whether a shoulder stability enhancement surgery that includes a bone graft is recommended for the patient. In some examples, the computing system may recommend a particular type of procedure to enhance stability of the shoulder.

In one example, this disclosure describes a method comprising: determining, by a computing system, a first areal size as an areal size of a predicted premorbid glenoid bone of a patient; determining, by the computing system, a second areal size as an areal size of a Bankart lesion on a morbid glenoid bone of the patient; determining, by the computing system, a third areal size as an areal size of a geodesic surface on a 3-dimensional (3D) model of a predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein: the projected medial border of the Hill-Sachs lesion is a projection of a medial border of Hill-Sachs lesion onto the 3D model of the predicted premorbid humerus, and the projected medial border of the footprint of the humeral head of the morbid humerus is a projection of a medial border of the footprint of the humeral head of the morbid humerus onto the 3D model of the predicted premorbid humerus; determining, by the computing system, based on the first, second, and third areal sizes, whether bone loss of the patient involves joint engagement; and based on a determination that the bone loss of the patient involves joint engagement, outputting, by the computing system, an indication that a shoulder stability enhancement surgery that includes a bone graft is recommended for the patient.

In another example, this disclosure describes a computing system comprising: a memory configured to store data describing a 3-dimensional (3D) model of a predicted premorbid humerus of a patient; and processing circuitry configured to: determine a first areal size as an areal size of a predicted premorbid glenoid bone of the patient of the patient; determine a second areal size as an areal size of a Bankart lesion on a morbid glenoid bone of the patient; determine a third areal size as an areal size of a geodesic surface on the 3D model of the predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein: the projected medial border of the Hill-Sachs lesion is a projection of a medial border of Hill-Sachs lesion onto the 3D model of the predicted premorbid humerus, and the projected medial border of the footprint of the humeral head of the morbid humerus is a projection of a medial border of the footprint of the humeral head of the morbid humerus onto the 3D model of the predicted premorbid humerus; determine, based on the first, second, and third areal sizes, whether bone loss of the patient involves joint engagement; and based on a determination that the bone loss of the patient involves joint engagement, output an indication that a shoulder stability enhancement surgery that includes a bone graft is recommended for the patient.

In another example, this disclosure describes a computing system comprising: means for determining a first areal size as an areal size of a predicted premorbid glenoid bone of a patient; means for determining a second areal size as an areal size of a Bankart lesion on a morbid glenoid bone of the patient; means for determining a third areal size as an areal size of a geodesic surface on a 3-dimensional (3D) model of a predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein: the projected medial border of the Hill-Sachs lesion is a projection of a medial border of Hill-Sachs lesion onto the 3D model of the predicted premorbid humerus, and the projected medial border of the footprint of the humeral head of the morbid humerus is a projection of a medial border of the footprint of the humeral head of the morbid humerus onto the 3D model of the predicted premorbid humerus; means for determining, based on the first, second, and third areal sizes, whether bone loss of the patient involves joint engagement; and means for outputting, based on a determination that the bone loss of the patient involves joint engagement, an indication that a shoulder stability enhancement surgery that includes a bone graft is recommended for the patient.

The details of various examples of the disclosure are set forth in the accompanying drawings and the description below. Various features, objects, and advantages will be apparent from the description, drawings, and claims.

BRIEF DESCRIPTION OF DRAWINGS

FIG. 1A illustrates an example bone loss identification process in a 2-dimensional (2D) image of a humeral head of a patient.

FIG. 1B illustrates an example bone loss identification process in a 2D image of a glenoid bone.

FIG. 5 is a table for calculating an Instability Severity Index Score.

FIGS. 12A, 12B, 12C, and 12D are conceptual diagrams of an example of manual selection of points on a border of a Hill-Sachs lesion and points on a border of a footprint of a humeral head of a morbid humerus, in accordance with one or more aspects of this disclosure.

DETAILED DESCRIPTION

As briefly discussed above, shoulder instability refers to a variety of disorders that result in dislocation, subluxation, or a general lack of stability of the glenohumeral joint. Shoulder instability is frequently caused by trauma that forces the humeral head in an anterior direction relative to the glenoid bone. This disclosure uses the term "glenoid bone" to refer to a portion of the scapula that defines and surrounds the glenoid cavity of the scapula. As a result of the movement of the humeral head in the anterior direction relative to the glenoid bone, bone loss may develop on the humeral head and the glenoid bone. When there is anterior shoulder instability, the humeral head typically has posterolateral bone loss and the glenoid bone typically has anteroinferior bone loss. The bone loss on the humeral head may be referred to as a Hill-Sachs lesion. The bone loss on the glenoid bone may be referred to as a Bankart lesion.

The presence or absence of a Hill-Sachs lesion and/or a Bankart lesion, along with one or more size characteristics and positional characteristics of such lesions, may be used as a guide in planning a shoulder stability enhancement surgery. In other words, a decisional tree for planning a shoulder stability enhancement surgery may depend on the sizes and locations of the Hill-Sachs and Bankart lesions. Conventionally, the presence and characteristics of Hill-Sachs and Bankart lesions are determined using 2-dimensional (2D) scans or 3-dimensional (3D) reconstructed surfaces.

FIG. 1A illustrates an example bone loss identification process in a 2D image of a humeral head of a patient. To determine the size characteristics of a Hill-Sachs lesion, a set of 2D images is generated, e.g., using computed tomography (CT). Each of the 2D images is in a transverse plane of the patient. A surgeon may then select one of the 2D images and may then fit a circle 100 over a portion of the selected 2D image that corresponds to the humeral head. The size characteristics of the Hill-Sachs lesion may be identified based on the length of a chord (W) spanning the Hill-Sachs lesion and a depth (D) measured from a point on the circle to a deepest point of the Hill-Sachs lesion.

FIG. 1B illustrates an example bone loss identification process in a 2D image of a glenoid bone. To determine the size characteristics of a Bankart lesion, a set of 2D images are generated. Each of the 2D images is from a sagittal perspective. The surgeon may then select one of the 2D images and may fit a circle 102 over a portion of the selected 2D image that corresponds to the glenoid bone. In FIG. 1B, "a" denotes the diameter of circle 102 that is perpendicular to a surface of the glenoid bone. In FIG. 1B, "b" denotes a segment of the diameter "a" from circle 102 to the surface of the glenoid bone.

Figure 2B:
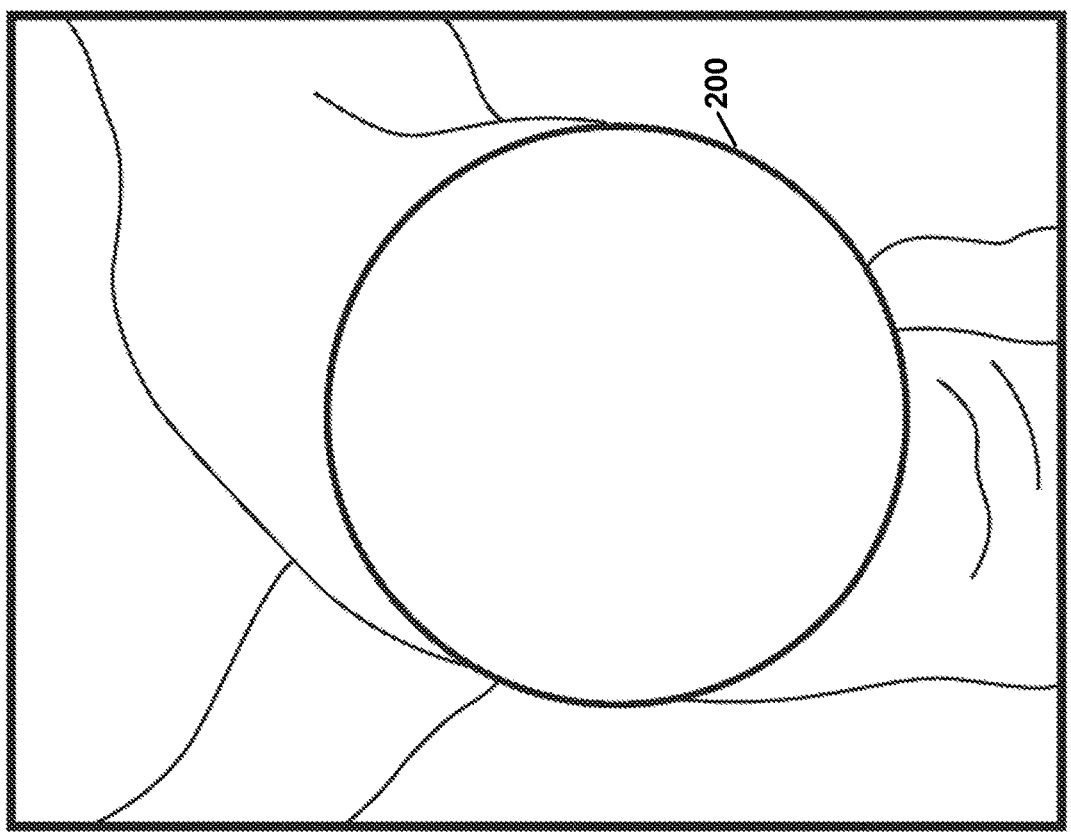
FIG. 2A and FIG. 2B illustrate an example bone loss identification process in 3D reconstructed surfaces.
Figure 2A:
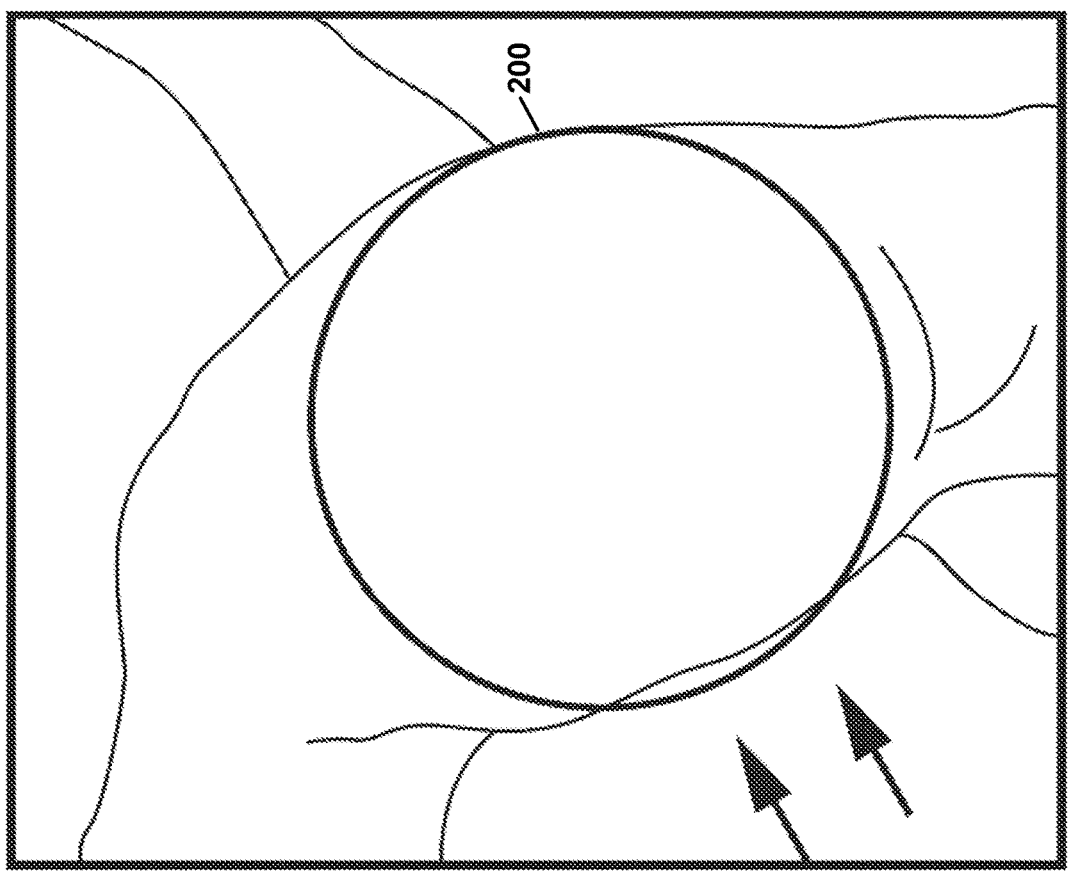

FIG. 2A and FIG. 2B illustrate an example bone loss identification process in 3D reconstructed surfaces. In the example of FIG. 2A and FIG. 2B, a 3D model of a glenoid bone of a patient is reconstructed, e.g., based on CT images of the patient. A surgeon may then rotate the 3D model to an appropriate position and fit a circle 200 over a portion of the 3D model that corresponds to a border of the glenoid cavity. The surgeon may then determine a depth of the Bankart lesion as a size of a gap between the circle and a surface of the model, as indicated by the white arrows in FIG. 2A. However, it is noted that if the 3D model of the glenoid bone is rotated slightly, as shown in FIG. 2B, the gap is not visible.

Both the technique shown in FIG. 1A and FIG. 1B and the technique shown in FIG. 2A and FIG. 2B are prone to error. For instance, errors may result from the technique shown in FIG. 1A and FIG. 1B if the patient is not perfectly oriented during imaging, because the surgeon selects a suboptimal 2D image, because the surgeon selects a suboptimal position for the width, or because of other operator errors. Furthermore, errors may result from the technique shown in FIG. 2A and FIG. 2B because the surgeon rotates the 3D model to a suboptimal position.

Figure 3:
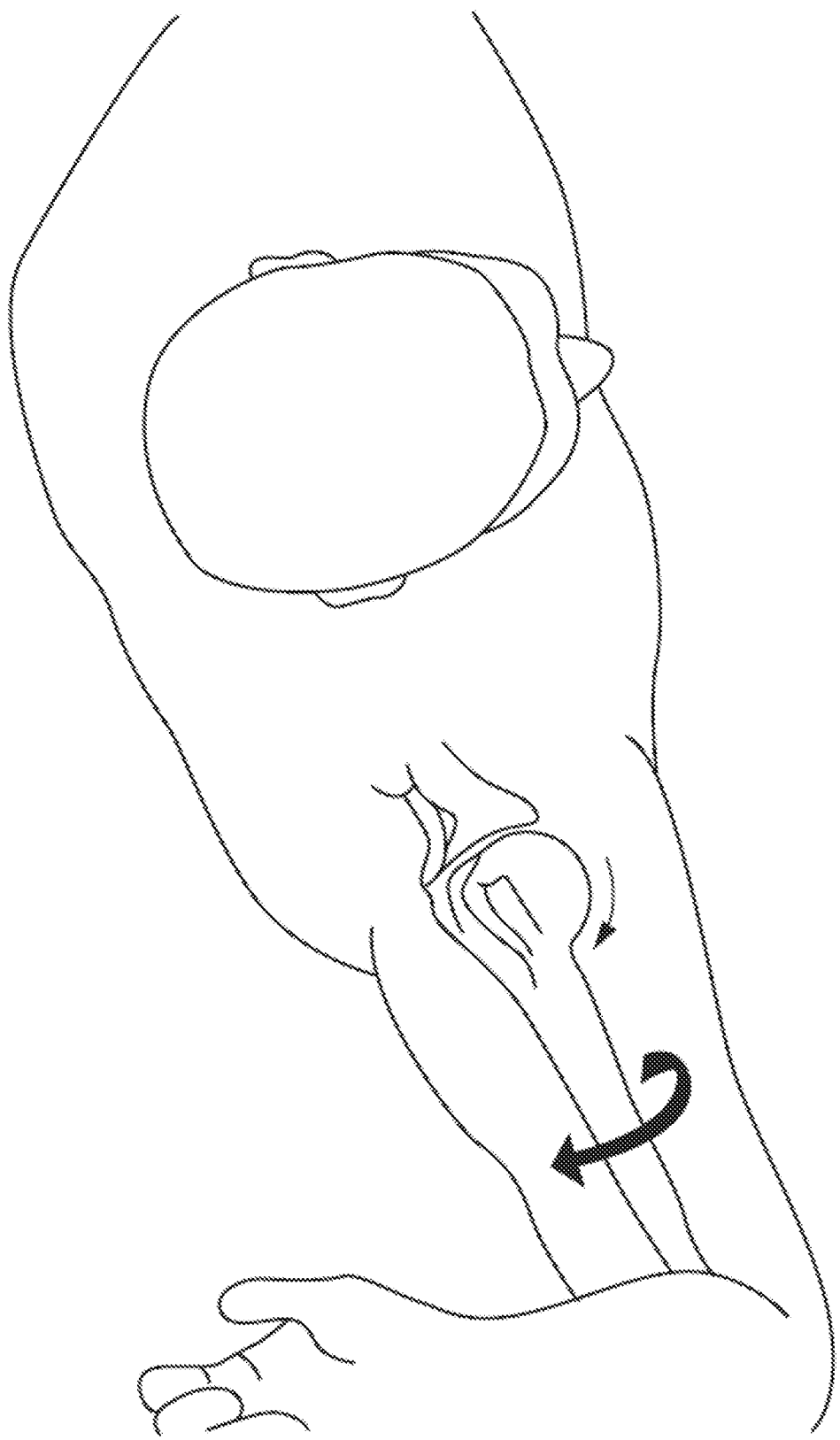
FIG. 3 illustrates a superior view of abduction and external rotation of the shoulder.

In addition to determining the presence of Hill-Sachs and Bankart lesions and their size characteristics, it may be informative to determine whether recurrent subluxation of the humeral head occurs when the patient performs an abduction and external rotation movement of the shoulder. FIG. 3 illustrates a superior view of abduction and external rotation of the shoulder. If recurrent subluxation of the humeral head occurs when the patient performs the abduction and external rotation movement of the shoulder, the glenohumeral joint is said to be "engaging," "involving joint engagement," or "off-track." In contrast, if recurrent subluxation of the humeral head does not occur when the patient performs this movement, the glenohumeral joint is said to be the "non-engaging" or "on-track." Recurrent subluxation of the humeral head when the patient performs the abduction and external rotation movement is likely to occur due to the presence of Bankart and/or Hill-Sachs lesions.

Itoi et al., "'On-track' and 'offtrack' shoulder lesions," EFORT Open Rev. 2017 Aug. 1; 2(8):343-351. doi: 10.1302/2058-5241.2.170007. eCollection 2017 August. Review (hereinafter, "Itoi") describes a formula for identifying, from the size characteristics of the Hill-Sachs and Bankart lesions, whether the glenohumeral joint is engaging or non-engaging. In other words, Itoi describes an approach to identify engaging joints. The approach described by Itoi uses one-dimensional values and depends on multiple parameters.

Particularly, there are three parameters in the approach described by Itoi. A first parameter is a premorbid glenoid width. In the example of FIG. 1B, "a" denotes premorbid glenoid width. A second parameter is the glenoid bone loss width. In the example of FIG. 1B, "b" denotes the glenoid bone loss width. The glenoid bone loss width may be determined as a distance from a point on the circle to the bone surface. A third parameter is a distance between a medial border of the humeral lesion (i.e., a Hill-Sachs lesion) and a most medial point on a footprint of a humeral head of the humerus. The footprint of the humeral head may be considered to be a plane that defines an interface between the humeral head and the rest of the humerus. The footprint of the humeral head is defined between the humeral head and the major and minor tuberosities of the humerus. The footprint of the humeral head typically corresponds to a limit of the humeral head that may slide against the glenoid cavity, in a premorbid state.

Figure 4:
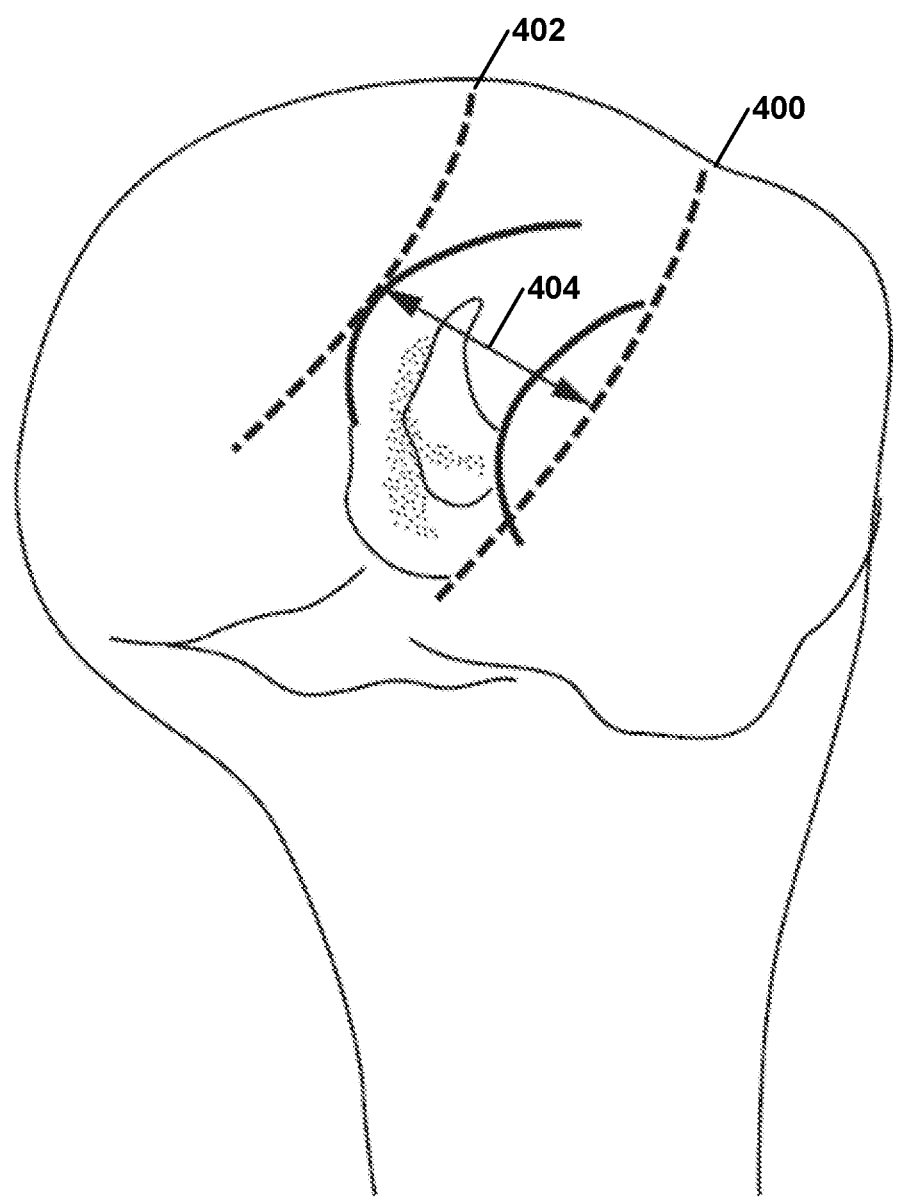
FIG. 4 illustrates an example humeral head footprint border and a Hill-Sachs lesion border.

FIG. 4 illustrates an example humeral head footprint border and a Hill-Sachs lesion border. Particularly, in the example of FIG. 4, line 400 indicates the medial border of the footprint of the humeral head. Line 402 indicates a medial border of the Hill-Sachs lesion. Arrow 404 indicates the distance between the medial border of the Hill-Sachs lesion and the most medial point on the footprint of the humeral head.

The approach described by Itoi assumes that 83% of glenohumeral contact is covered by the glenoid cavity during abduction and external rotation movement of the shoulder. Furthermore, Itoi indicates that the following inequality applies when the glenohumeral joint is engaging:

$$((0.83 \times a) - b) > c$$

In the inequality above, a denotes the first parameter (i.e., premorbid glenoid width), b denotes the second parameter (i.e., glenoid bone loss width), and c denotes the third parameter (i.e., a distance between a medial border of the humeral lesion (i.e., a Hill-Sachs lesion) and a most medial point on a footprint of a humeral head of the humerus). Similarly, Itoi indicates that the following inequality applies when the glenohumeral joint is non-engaging:

$$0.83 \times a - b \leq c$$

In the inequality above, a denotes the first parameter, b denotes the second parameter, and c denotes the third parameter.

Furthermore, when a surgeon is planning a shoulder stability enhancement surgery, the surgeon may calculate an Instability Severity Index Score (ISIS) for a patient. FIG. 5 is a table for calculating an ISIS for a patient. In FIG. 5, "AP" denotes anteroposterior. An ISIS for a patient is an estimate of a risk that the patient will experience a recurrence of a shoulder instability condition. A patient with a higher ISIS is at greater risk of experiencing a recurrence of a shoulder instability condition than a patient with a lower ISIS. The risk that the patient will experience a recurrence of the shoulder instability condition may guide the surgeon when choosing a surgical procedure to perform on the patient.

In accordance with one or more techniques of this disclosure, a 3D ISIS for a patient may be determined for a patient instead of the ISIS illustrated in the example of FIG. 5. The 3D ISIS may use the same age, degree of sport participation, type of sport, and shoulder hyperlaxity aspects of the ISIS calculation of FIG. 5. However, with respect to the Hill-Sachs component of the 3D ISIS, one or more point values associated with a 3D shape and/or volume of the Hill-Sachs lesion may be determined. For instance, in one example, the 3D volume of the Hill-Sachs lesion may be assigned a point value. In some examples, a length, width, and depth of the Hill-Sachs lesion may be determined. For each of the length, width, and depth of the Hill-Sachs lesion, a point value ranging from 0 to 3 is determined.

Similarly, in determining the 3D ISIS for the patient, one or more point values may be determined based on the 3D shape and/or volume of glenoid loss. For example, losses to the glenoid bone may be assigned a point value. In some examples, each of a length, width, and depth of a Bankart lesion may be assigned a point value.

The point values, including the point values for the Hill-Sachs lesion and glenoid bone loss, may then be totaled to determine the 3D ISIS. Use of the 3D ISIS may provide more direct and accurate guidance to surgeons than the ISIS illustrated in the example of FIG. 5. For instance, with respect to the example of FIG. 6, the surgeon or computing system may be more likely to select the correct surgical procedure.

Figure 6:
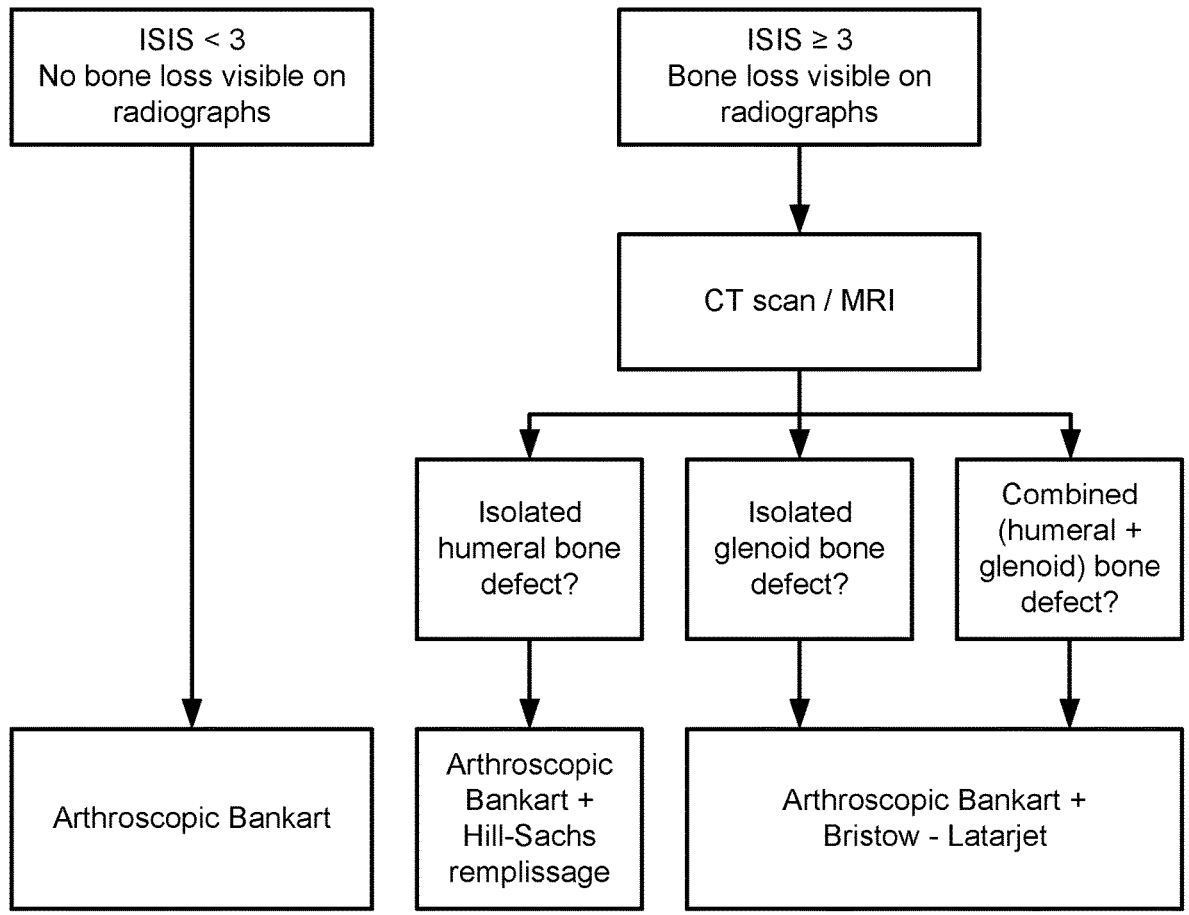
FIG. 6 is a decision tree for selecting a surgical procedure to enhance shoulder stability.

FIG. 6 is a decision tree for selecting a surgical procedure to enhance shoulder stability. In the example of FIG. 6, if the ISIS for a patient is less than 3, the recommended surgical option is an arthroscopic Bankart surgery. The arthroscopic Bankart surgery repairs tissue covering a Bankart lesion and does not involve a bone graft. For instance, during an arthroscopic Bankart surgery, the surgeon may reconnect tissue such that the Bankart lesion is no longer exposed.

On the other hand, if the ISIS for the patient is greater than or equal to 3, the surgeon may order a CT scan or magnetic resonance imaging (MRI). 2D images or 3D models, such as those shown in FIG. 1A, FIG. 1B, FIG. 2A, and FIG. 2B, may be generated as a result of such a CT scan or MRI. The surgeon may then use the resulting 2D images or 3D models to determine whether the patient has an isolated humeral bone defect, an isolated glenoid bone defect, or both a humeral bone defect and a glenoid bone defect. If the patient has an isolated humeral defect (e.g., the patient has a Hill-Sachs lesion and not a Bankart lesion), the recommended surgical option may be an arthroscopic Bankart surgery with a Hill-Sachs remplissage surgery. During the Hill-Sachs remplissage surgery, the surgeon fills in the Hill-Sachs lesion with tendon tissue. However, if the patient has an isolated glenoid bone defect (e.g., the patient has a Bankart lesion and not a Hill-Sachs lesion) or the patient has a combination a humeral bone defect and a glenoid bone defect (e.g., the patient has a Bankart lesion and a Hill-Sachs lesion), the recommended surgical option may be an arthroscopic Bankart surgery and, possibly, a Bristow surgery or Latarjet surgery. In cases where the patient's bone loss involves joint engagement, the Bristow surgery or the Latajet surgery may be recommended. However, if the patient has an isolated glenoid bone defect or the patient has a combination of a humeral bone defect and a glenoid bone defect, but the bone loss does not involve joint engagement, the Bristow surgery or Latarjet surgery may not be recommended. During the Bristow or Latarjet surgeries, the surgeon removes a piece of the patient's coracoid process and attaches the removed piece of the patient's coracoid process to a prepared area of the glenoid bone. This may help stop the humeral head from sliding out of the glenoid cavity in an anterior direction.

In examples where 3D ISIS is used, a CT scan or MRI of a patient may be performed before calculating the 3D ISIS of the patient. If the 3D ISIS for the patient is less than 6, the recommended surgical option is the arthroscopic Bankart surgery. Otherwise, a process to determine among an arthroscopic Bankart plus Hill-Sachs remplissage, or arthroscopic Bankart plus Bristow or Latarjet surgery may be performed.

Decision trees other than those shown in the example of FIG. 6 may be applied. For instance, Ramhamadany et al., "Current concepts in the management of recurrent anterior gleno-humeral joint instability with bone loss," World J Orthop., Jun. 18, 2016; 7(6): 343-354, describes a decision tree in which the ISIS may be used as part of a process to determine whether to select an open reduction and internal fixation surgery or a Latarjet surgery. In this example, the 3D ISIS may be used in place of the ISIS calculated using the table of FIG. 5. Another decision tree that uses ISIS is described in Özturk et al., "Prise en charge d'un premier épisode de luxation antéro-inférieure de l'épaule chez l'athlète," Rev Med Suisse 2018; volume 14. 1326-1331. The ISIS used in the decision tree of Özturk may be replaced with the 3D ISIS described elsewhere in this disclosure.

As noted above, current processes for planning surgeries to enhance shoulder stability may be laborious for surgeons and may be prone to errors. Such errors may cause surgeons to arrive at incorrect conclusions about the types of surgery to perform. For example, current processes may require the surgeon to manually determine amounts of bone loss and manually determine whether a Hill-Sachs lesion on a humerus head engages the glenoid during abduction and external rotation of glenohumeral joint. These determinations are subject to human error and may be dependent on correct orientation of a patient during 2-dimensional imaging and/or correct positioning of a 3-dimensional model.

Figure 7:
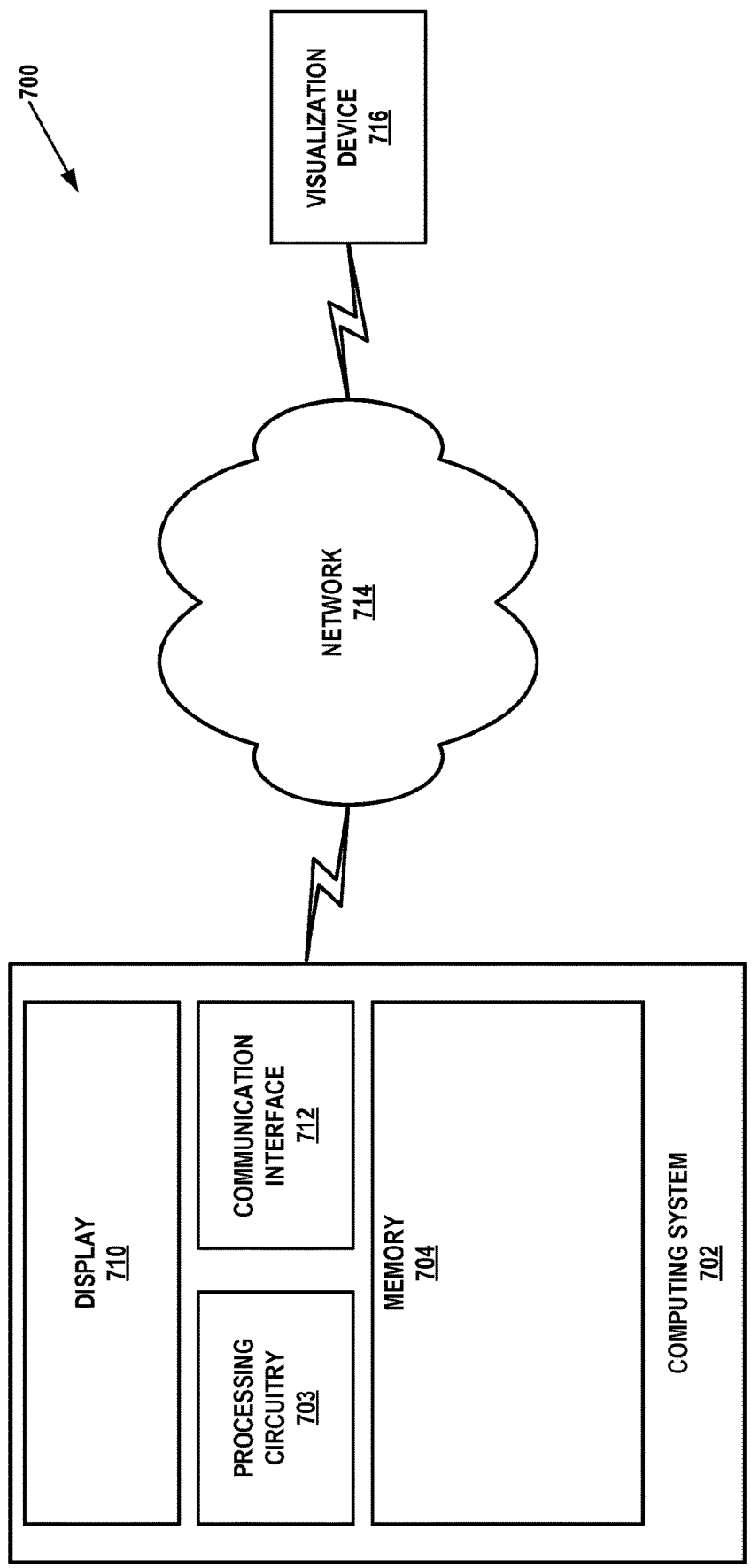
FIG. 7 is a block diagram illustrating an example system that may be used to implement the techniques of this disclosure.

The techniques of this disclosure may apply computational techniques to improve the predictability and accuracy of certain aspects of the planning process for shoulder stability enhancement surgeries. FIG. 7 is a block diagram illustrating an example system 700 that may be used to implement the techniques of this disclosure. FIG. 7 illustrates computing system 702, which is an example of a computing system configured to perform one or more example techniques described in this disclosure. Computing system 702 may include various types of computing devices, such as server computers, personal computers, smartphones, laptop computers, and other types of computing devices. Computing system 702 includes processing circuitry 703, memory 704, and display 710. Display 710 is optional, such as in examples where computing system 702 comprises a server computer.

Examples of processing circuitry 703 include one or more microprocessors, digital signal processors (DSPs), application specific integrated circuits (ASICs), field programmable gate arrays (FPGAs), hardware, or any combinations thereof. In general, processing circuitry 703 may be implemented as fixed-function circuits, programmable circuits, or a combination thereof. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more of the units may be distinct circuit blocks (fixed-function or programmable), and in some examples, the one or more units may be integrated circuits.

Processing circuitry 703 may include arithmetic logic units (ALUs), elementary function units (EFUs), digital circuits, analog circuits, and/or programmable cores, formed from programmable circuits. In examples where the operations of processing circuitry 703 are performed using software executed by the programmable circuits, memory 704 may store the object code of the software that processing circuitry 703 receives and executes, or another memory within processing circuitry 703 (not shown) may store such instructions. Examples of the software include software designed for surgical planning. Processing circuitry 703 may perform the actions ascribed in this disclosure to computing system 702.

Memory 704 may store various types of data used by processing circuitry 703. For example, memory 704 may store data describing 3D models of various anatomical structures, including morbid and predicted premorbid anatomical structures. For instance, in one specific example, memory 704 may store data describing a 3D model of a predicted premorbid humerus of a patient.

Memory 704 may be formed by any of a variety of memory devices, such as dynamic random access memory (DRAM), including synchronous DRAM (SDRAM), magnetoresistive RAM (MRAIVI), resistive RAM (RRAM), or other types of memory devices. Examples of display 710 include a liquid crystal display (LCD), a plasma display, an organic light emitting diode (OLED) display, or another type of display device.

Computing system 702 may include a communication interface 712 that allows computing system 702 to output data and instructions to and receive data and instructions from visualization device 716 via a network 714. Communication interface 712 may be hardware circuitry that enables computing system 702 to communicate (e.g., wirelessly or using wires) to other computing systems and devices, such as visualization device 716. Network 714 may include various types of communication networks including one or more wide-area networks, such as the Internet, local area networks, and so on. In some examples, network 714 may include wired and/or wireless communication links.

Visualization device 716 may utilize various visualization techniques to display image content to a surgeon. Visualization device 716 may be a mixed reality (MR) visualization device, virtual reality (VR) visualization device, holographic projector, or other device for presenting extended reality (XR) visualizations. In some examples, visualization device 716 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Visualization device 716 may utilize visualization tools that are available to utilize patient image data to generate three-dimensional models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system available from Wright Medical Technology, Inc. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system may be compiled in a preoperative surgical plan for the patient that is stored in a database at an appropriate location (e.g., on a server in a wide area network, a local area network, or a global network) where it can be accessed by the surgeon or other care provider, including before and during the actual surgery.

Figure 8:
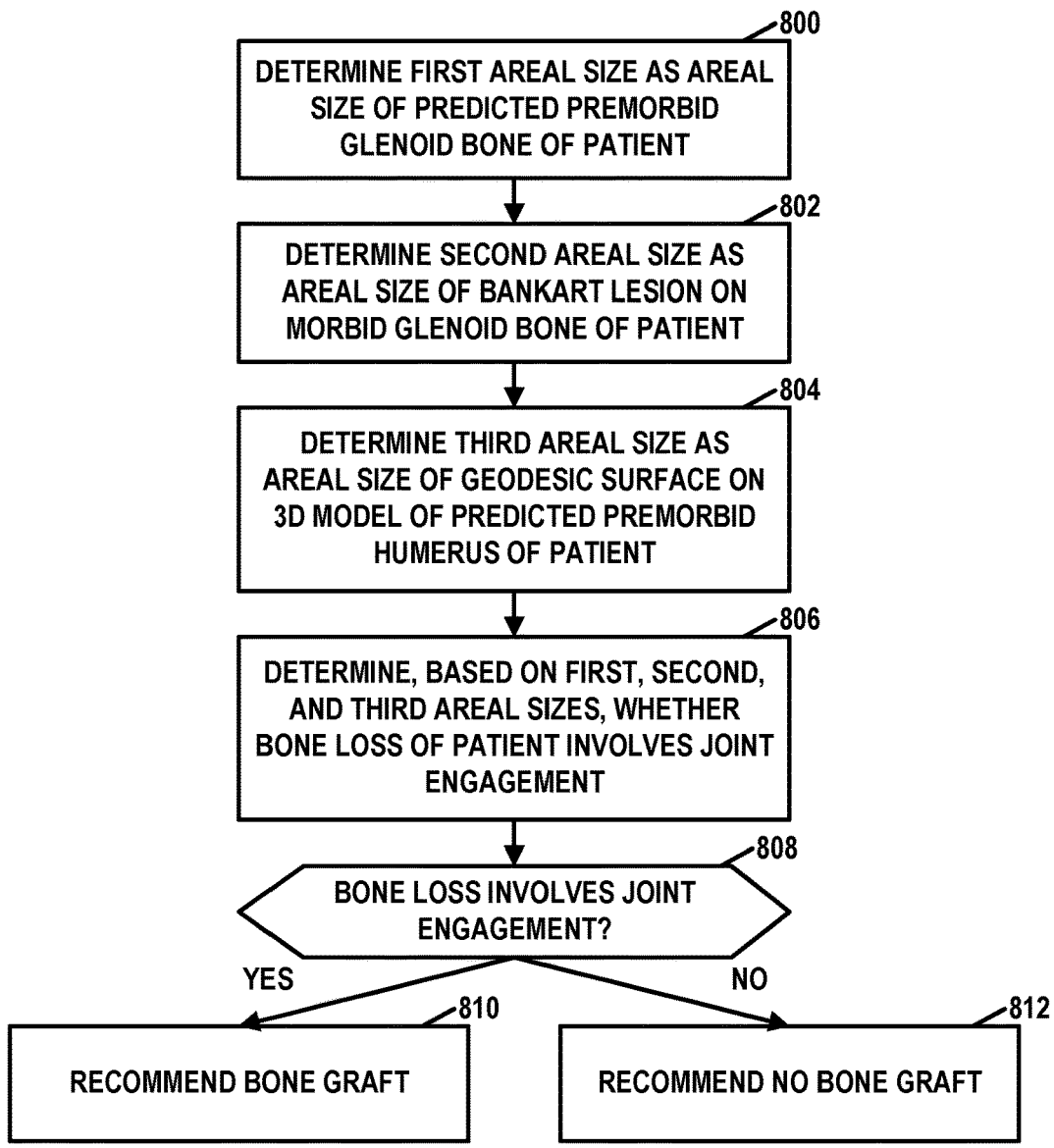
FIG. 8 is a flowchart illustrating an example operation of the computing system, in accordance with one or more aspects of this disclosure.

FIG. 8 is a flowchart illustrating an example operation of the computing system, in accordance with one or more aspects of this disclosure. The flowcharts of this disclosure are provided as examples. Other example operations may include more, fewer, or different actions, or actions may be performed in different orders or in parallel.

In the example of FIG. 8, computing system 702 may determine a first areal size as an areal size of a predicted premorbid glenoid bone of the patient (800). Computing system 702 may determine the predicted premorbid glenoid bone in one or more of various ways. For example, computing system 702 may determine a 3D model of a predicted premorbid glenoid bone using any of the examples described in PCT Application PCT/US2020/023361, entitled "PRE-MORBID CHARACTERIZATION OF ANATOMICAL OBJECT USING STATISTICAL SHAPE MODELING (SSM)" and filed Mar. 18, 2020, or PCT Application PCT/US/2020/023358, entitled "PRE-MORBID CHARACTERIZATION OF ANATOMICAL OBJECT USING STATISTICAL SHAPE MODELING (SSM)" and filed Mar. 18, 2020, the contents of both applications are incorporated herein by reference.

For example, similar to the techniques described in PCT Application PCT/US2020/023361, computing system 702 may determine the areal size of the predicted premorbid glenoid bone by using statistical shape modelling (SSM) and imaging data (e.g., CT data) of the current anatomy of the patient. Computing system 702 may align an initial shape of the glenoid bone to segmented imaging data and may then deform the initial shape (e.g., adjusting the size, shape, and/or location with respect to the imaging data) through an iterative process that eventually registers the deformed initial shape to the target structure (e.g., the bone) from the segmented imaging data. This resulting final shape may be used as the predicted premorbid glenoid bone. In other examples, computing system 702 may register a mean statistical shape model (e.g., a model of the mean shape of the glenoid for a population of patients) to the imaging data for the patient. Then, computing system 702 may adjust the scale of the mean statistical shape model until a cost function of the difference between the mean statistical shape model and the glenoid of patient's imaging data is below a threshold (e.g., minimized). In either example, computer system 702 may determine a 3D model of a predicted premorbid glenoid bone for the patient.

Additionally, computing system 702 may determine a second areal size as an areal size of a Bankart lesion on a morbid glenoid bone of the patient (802). FIG. 9, which is described in greater detail elsewhere in this disclosure, describes a technique for determining the second areal size.

Furthermore, computing system 702 may determine a third areal size as an areal size of a geodesic surface on a 3D model of a predicted premorbid humerus of the patient (804). The geodesic surface is defined at least in part by (i) a projected medial border of a Hill-Sachs lesion on a morbid humerus and (ii) a projected medial border of a footprint of a humeral head of the morbid humerus. The projected medial border of the Hill-Sachs lesion is a projection of a medial border of Hill-Sachs lesion onto the 3D model of the predicted premorbid humerus. The projected medial border of the footprint of the humeral head of the morbid humerus is a projection of a medial border of the footprint of the humeral head of the morbid humerus onto the 3D model of the predicted premorbid humerus. In some examples, computing system 702 may determine the 3D model of a predicted premorbid humerus using any of the examples described in PCT Application PCT/US2020/023361, or PCT Application PCT/US2020/023358, incorporated by reference herein and as discussed above.

For example, similar to the techniques described in PCT Application PCT/US2020/023361, computing system 702 may determine the areal size of the predicted premorbid humerus by using statistical shape modelling (SSM) and imaging data (e.g., CT data) of the current anatomy of the patient. Computing system 702 may align an initial shape of the humerus to segmented imaging data and may then deform the initial shape (e.g., adjusting the size, shape, and/or location with respect to the imaging data) through an iterative process that eventually registers the deformed initial shape to the target structure (e.g., the bone) from the segmented imaging data. This resulting final shape may be used as the predicted premorbid humerus. In other examples, computing system 702 may register a mean statistical shape model (e.g., a model of the mean shape of the humerus for a population of patients) to the imaging data for the patient. Then, computing system 702 may adjust the scale of the mean statistical shape model until a cost function of the difference between the mean statistical shape model and the humerus of patient's imaging data is below a threshold (e.g., minimized). In either example, computer system 702 may determine a 3D model of a predicted premorbid humerus for the patient.

Computing system 702 may determine the third areal size in one of various ways. For instance, in one example, the 3D model of the predicted premorbid humerus of the patient may be represented as a mesh of triangle having 3-dimensional vertices. In this example, computing system 702 may determine the third areal size as a sum of the areas of the triangles.

Computing system 702 may determine, based on the first, second, and third areal sizes, whether bone loss of the patient involves joint engagement (806). For example, computing system 702 may apply the following equation to determine a track index:

$$T_{idx} = (0.83 \times A) - B - C$$

In the equation above, Lax denotes the track index, A denotes the first areal size, B denotes the second areal size, and C denotes the third areal size. Positive values of the track index correspond to non-engagement of the glenohumeral joint. Negative values of the track index correspond to engagement of the glenohumeral joint. Thus, in this example, as part of determining whether the bone loss of the patient involves joint engagement, computing system 702 may determine an index value ($T_{idx}$) as a predetermined percentage value (e.g., an assumed percentage of the glenoid cavity covered by the humeral head during abduction and external rotation movement of the shoulder) multiplied by the first areal size, minus the second areal size. Computing system 702 may then determine whether the bone loss of the patient involves joint engagement based on whether the index value is greater than or less than the third areal value.

If the bone loss of the patient involves joint engagement ("YES" branch of 808), computing system 702 may output an indication that a shoulder stability enhancement surgery that includes a bone graft is recommended for the patient (810). For instance, computing system 702 may recommend performance of a Bristow or Latarjet surgery. On the other hand, if the bone loss of the patient does not involve joint engagement ("NO" branch of 808), computing system 702 may output an indication that a shoulder stability enhancement surgery that does not include a bone graft is recommended (812).

Figure 9A:
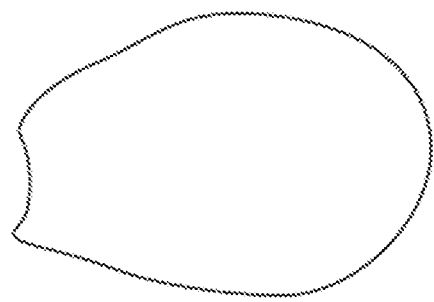
FIGS. 9A, 9B, 9C, 9D, 9E, and 9F are conceptual diagrams of an example process for identifying glenoid bone loss, in accordance with one or more aspects of this disclosure.
Figure 9B:
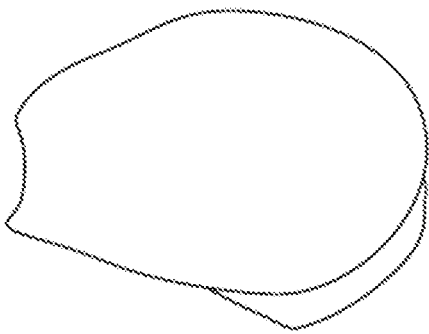
Figure 9C:
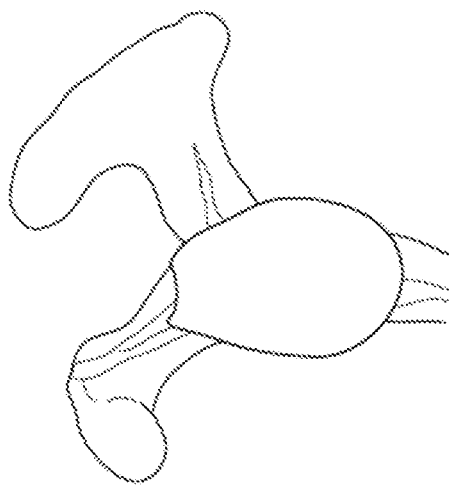

FIG. 9A through FIG. 9F are conceptual diagrams of an example process for identifying glenoid bone loss, in accordance with one or more aspects of this disclosure. As noted above with respect to FIG. 8, computing system 702 may determine an areal size of a Bankart lesion on a morbid glenoid bone of the patient. To determine the areal size of the Bankart lesion, computing system 702 may generate a 3D model of the morbid glenoid bone (FIG. 9A). Computing system 702 may generate the 3D model of the morbid glenoid bone based on CT images or an MRI scan of the patient according to conventional techniques for generating 3D models from CT images or an MM scan. FIG. 9B indicates the glenoid bone on the 3D model of the morbid glenoid bone. In some examples, computing system 702 may determine the outline of the morbid glenoid bone using an algorithm that, for each of several iterations corresponding to different radial directions, starts at a center of the glenoid and follows a path starting in the corresponding radial direction over the 3D model of the morbid glenoid bone until points at which medial values stop increasing. In this example, computing system 702 may interpolate between the points to define the outline of the glenoid bone. In other examples, computing system 702 may use other algorithms to determine the outline of the glenoid bone on the 3D model of the morbid glenoid bone. Additionally, computing system 702 may determine a projected morbid glenoid surface as a projection of the morbid glenoid bone onto a glenoid plane (FIG. 9C). The glenoid plane is a 2-dimensional plane. In some examples, the glenoid plane is oriented parallel to a sagittal plane of the patient. In some examples, the glenoid plane is a glenoid best-fit plane. The glenoid best-fit plane may be defined based on a border of the glenoid cavity.

Figure 9D:
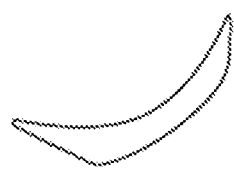

Computing system 702 may then determine a projected premorbid surface as a projection of the predicted premorbid glenoid bone onto the glenoid plane (FIG. 9D). When determining the first areal size (i.e., the areal size of a predicted premorbid glenoid bone of the patient), computing system 702 may determine the area of the projected premorbid surface. For example, computing system 702 may use a coordinate system to refer to points on the 3D model of the morbid glenoid bone. In this example, the y-axis of the coordinate system is normal to the glenoid plane of the patient. Accordingly, in this example, to determine the projection of the predicted premorbid glenoid bone onto the glenoid plane, computing system 702 may set the y-axis coordinates of all points in the 3D model of the morbid glenoid bone to the same predetermined value (e.g., 0).

Figure 9E:
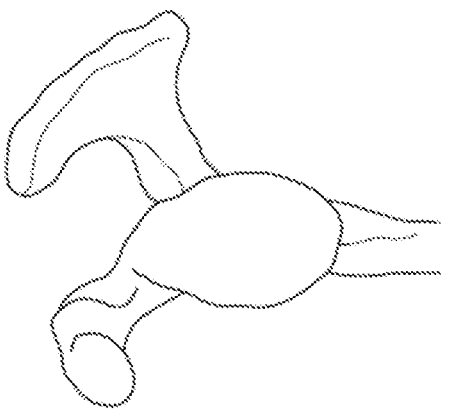
Figure 9F:
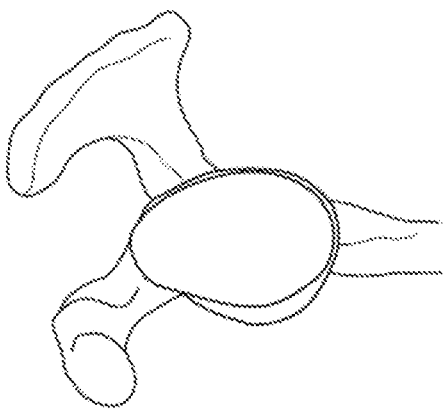

Additionally, computing system 702 may determine, based on the projected premorbid glenoid surface and the projected morbid glenoid surface, a zone of bone loss (FIG. 9E). The zone of bone loss may be defined as a primary area of non-intersection of the projected premorbid glenoid surface and the projected morbid glenoid surface. Computing system 702 may then determine the areal size of the Bankart lesion as the areal size of the zone of bone loss. FIG. 9F shows the zone of bone loss in combination with the projected morbid glenoid surface. Thus, in the example of FIGS. 9A-9F, computing system 702 may determine, based on a comparison of the 3D model of the morbid glenoid bone of the patient and a 3D model of the predicted premorbid glenoid bone, the areal size of the Bankart lesion on the morbid glenoid bone.

Thus, in the example of FIGS. 9A-9F, computing system 702 may determine a projected premorbid glenoid surface as a projection of the predicted premorbid glenoid bone onto a glenoid plane. Computing system 702 may also determine a projected morbid glenoid surface as a projection of the morbid bone of the patient onto the glenoid plane. Computing system 702 may then determine, based on the projected premorbid glenoid surface and the projected morbid glenoid surface, a zone of bone loss. Computing system 702 may determine the areal size of the Bankart lesion as an areal size of the zone of bone loss. For instance, computing system 702 may divide the polygon shown in FIG. 9E into a set of triangles, calculate the sizes of the triangles, and add the sizes of the triangles to determine the area of the Bankart lesion. A similar technique may be used in calculating areal sizes of other 2-dimensional surfaces in this disclosure.

Figure 10A:
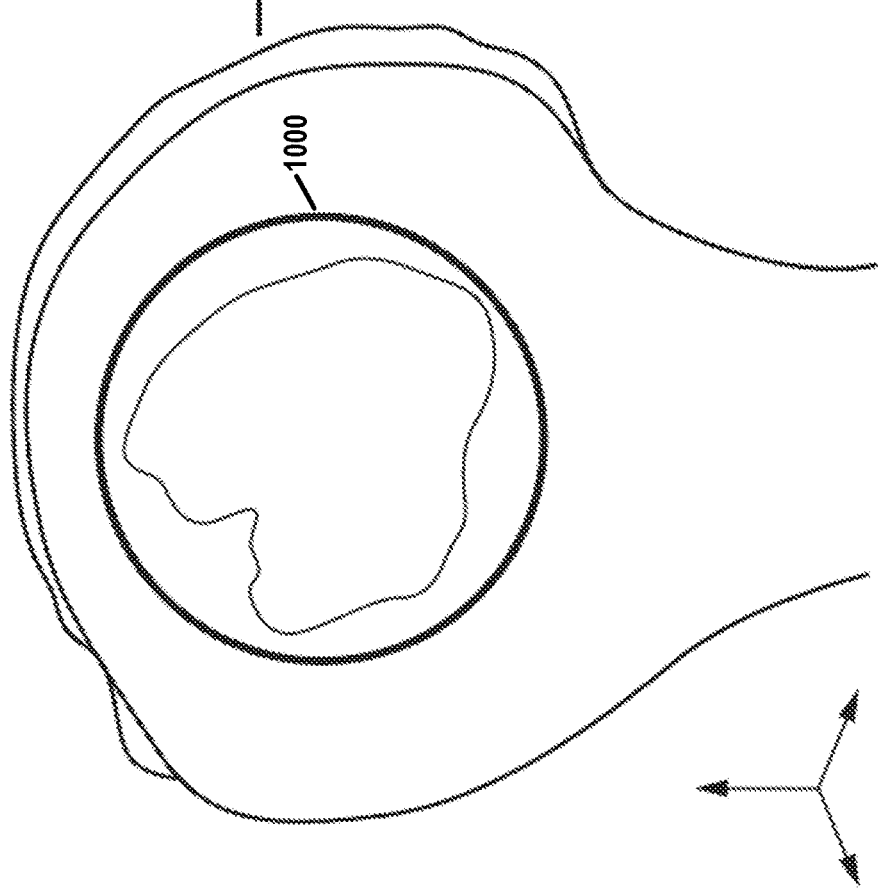
FIG. 10A is a conceptual diagram of an example 3D model of a morbid humerus and a corresponding 3D model of a predicted premorbid humerus, in accordance with one or more aspects of this disclosure.

FIG. 10A is a conceptual diagram of an example 3D model of a morbid humerus and a corresponding 3D model of a predicted premorbid humerus, in accordance with one or more aspects of this disclosure. In the example of FIG. 10A, circle 1000 indicates a general area of a Hill-Sachs lesion on a morbid humerus of a patient.

Figure 10B:
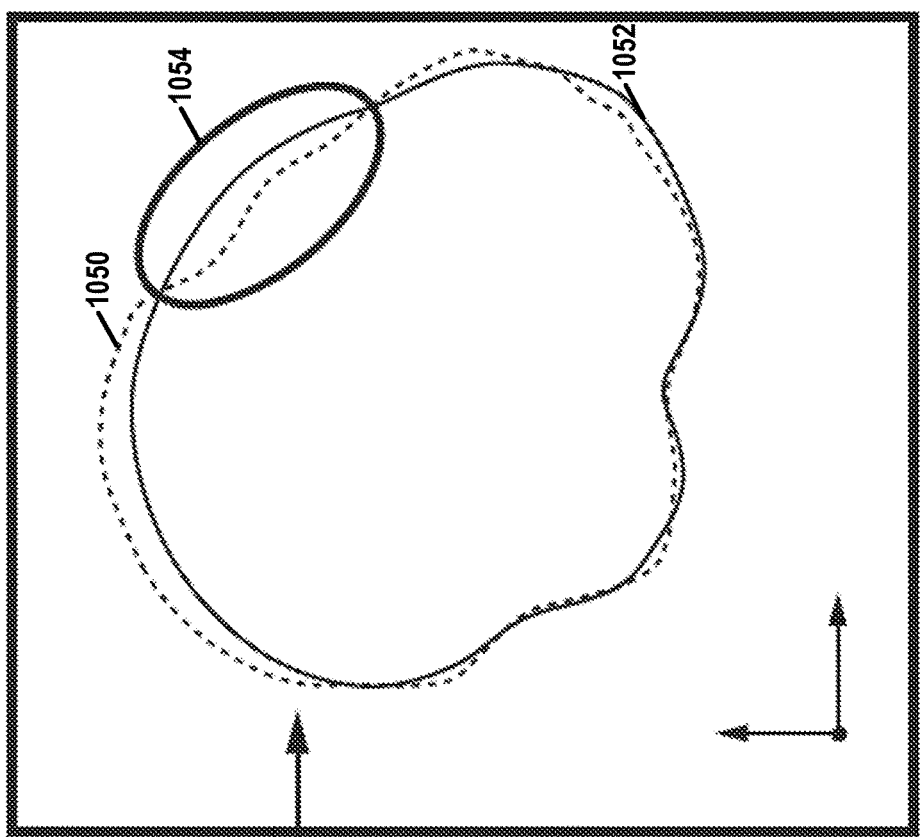
FIG. 10B is a conceptual diagram of an example 2D axial slice of the humerus showing posterior bone loss on a humeral head of the humerus.

FIG. 10B is a conceptual diagram of an example 2D axial slice of the humerus showing posterior bone loss on a humeral head of the morbid humerus. That is, FIG. 10B shows the humeral head of the morbid humerus from a perspective parallel to a long axis of the humerus. Particularly, in the example of FIG. 10B, line 1050 indicates an outline of the morbid humerus and line 1052 indicates an outline of a predicted premorbid humerus. Ellipse 1054 indicates a general position of the Hill-Sachs lesion.

Figure 11:
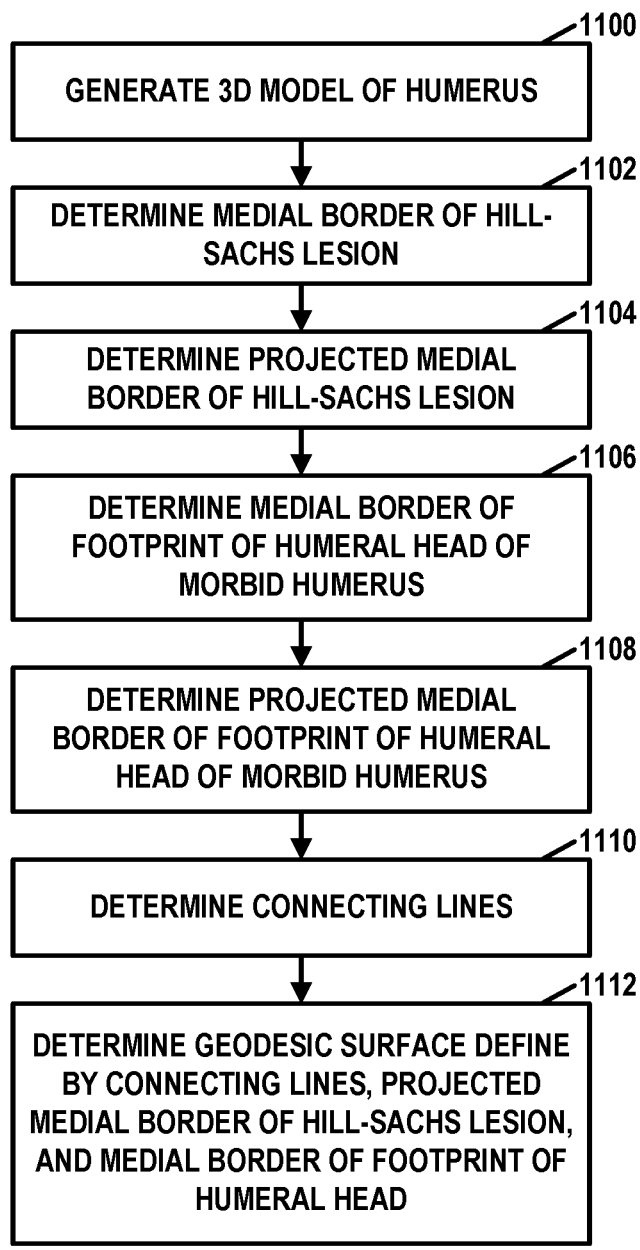
FIG. 11 is a flowchart illustrating an example operation of the computing system to determine a geodesic surface, in accordance with one or more aspects of this disclosure.

FIG. 11 is a flowchart illustrating an example operation of computing system 702 to determine a geodesic surface, in accordance with one or more aspects of this disclosure. As noted above, computing system 702 may determine a third areal size as an areal size of a geodesic surface on a 3D model of a predicted premorbid humerus of the patient. FIG. 11 represents one example of how to determine the third areal size.

Figure 13A:
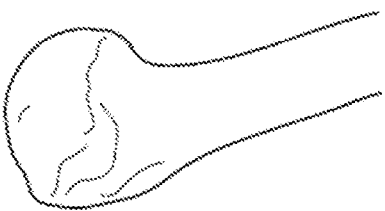
FIGS. 13A, 13B, 13C, 13D, 13E and 13F-13D are conceptual diagrams of an example operation to determine a geodesic surface, in accordance with one or more aspects of this disclosure.

In the example of FIG. 11, computing system 702 may generate a 3D model of the morbid humerus of a patient (1100). For instance, computing system 702 may generate the 3D model of the morbid humerus of the patient based on one or more CT images of the patient. FIG. 13A illustrates an example of a 3D model of a morbid humerus of a specific patient.

Figure 13B:
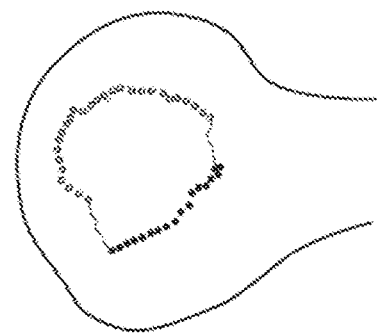
Figure 13C:
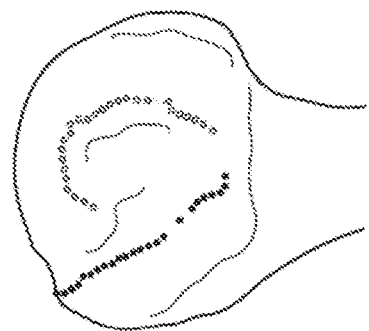

Additionally, in the example of FIG. 11, computing system 702 may determine a medial border of a Hill-Sachs lesion on the 3D model of the morbid humerus of the patient (1102). FIG. 13B illustrates a medial border of a Hill-Sachs lesion on the 3D model of the morbid humerus of the patient. Particularly, hollow dots in FIG. 13 indicate points along the medial border of the Hill-Sachs lesion.

Computing system 702 may determine the medial border of the Hill-Sachs lesion in one of various ways. In some examples, computing system 702 may determine the medial border of the Hills-Sachs lesion automatically. For instance, computing system 702 may apply an algorithm that identifies discontinuities in the slope of the surface of the humeral head. In some examples, to determine the medial border of the Hill-Sachs lesion on the 3D model of the morbid humerus of the patient, computing system 702 may output the 3D model of the morbid humerus for display. For instance, computing system 702 may output the 3D model of the morbid humerus for display on a display screen or as a mixed reality (MR) or virtual reality (VR) visualization. Additionally, in this example, computing system 702 may receive indications of user input of a set of points 1200 along the medial border of the Hill-Sachs lesion on the 3D model of the morbid humerus. FIG. 12C is a conceptual diagram indicating points on a 3D model of a morbid humerus along the medial border of the Hill-Sachs lesion. In this example, computing system 702 may then interpolate, based on points 1200, the medial border of the Hill-Sachs lesion on the 3D model of the morbid humerus. FIG. 12D also shows points on a full border of the Hill-Sachs lesion.

Furthermore, in the example of FIG. 11, computing system 702 may determine a projected medial border of the Hill-Sachs lesion as the projection of the medial border of the Hill-Sachs lesion onto the 3D model of the predicted premorbid humerus (1104). For example, computing system 702 may take the medial border of the Hill-Sachs lesion and copy it onto a corresponding location on a surface of the 3D model of the predicted premorbid humerus. In some examples, to determine the projected medial border of the Hill-Sachs lesion, computing system 702 may determine, for each point in a set of points on the medial border of the Hill-Sachs lesion, a closest corresponding point on the 3D model of the predicted premorbid humerus. In this example, computing system 702 may then determine a path connecting the corresponding points on the 3D model of the predicted premorbid humerus (e.g., using the Dijkstra algorithm to determine the shortest geodesic path through the corresponding points on the 3D model of the predicted premorbid humerus). Computing system 702 may determine the 3D model of the predicted premorbid humerus using any of the examples described in PCT Application PCT/US2020/023361, or PCT Application PCT/US2020/023358, incorporated by reference herein and as discussed above.

Additionally, computing system 702 may determine a medial border of the footprint of the humeral head of the morbid humerus (1106). In some examples, computing system 702 may determine the medial border of the footprint of the humeral head automatically. For instance, in one example, computing system 702 may apply an algorithm that identifies discontinuities in the slope of the 3D model of the morbid humerus at an edge of the humeral head. In this example, a line of such discontinuities may correspond to the medial border of the footprint of the humeral head.

In some examples, to determine the medial border of the footprint of the humeral head of the morbid humerus, computing system may output the 3D model of the morbid humerus for display. For instance, computing system 702 may output the 3D model of the morbid humerus for display on a display screen or as a MR or VR visualization. Additionally, in this example, computing system 702 may receive indications of user input of a set of points along the medial border of the footprint of the humeral head of the morbid humerus. FIG. 12A, FIG. 12B, and FIG. 12D are conceptual diagrams indicating points 1202 on a 3D model of a morbid humerus along the medial border of the footprint of the humeral head of the morbid humerus. In this example, computing system 702 may then interpolate, based on points 1202, the medial border of the footprint of the humeral head of the morbid humerus.

Furthermore, in the example of FIG. 11, computing system 702 may determine the projected medial border of the footprint of the humeral head of the morbid humerus as the projection of the medial border of the footprint of the humeral head of the morbid humerus onto the 3D model of the predicted premorbid humerus (1108). Computing system 702 may determine the projected medial border of the footprint of the humeral head in much the same way as computing system 702 determines the projected medial border of the Hill-Sachs lesion.

Computing system 702 may then determine connecting lines that connect the projected medial border of the Hill-Sachs lesion and the projected medial border of the footprint of the humeral head of the morbid humerus (1110). The connecting lines may be the shortest geodesic paths over the 3D model of the predicted premorbid humerus from points on the projected medial border of the Hill-Sachs lesion to points on the projected medial border of the footprint of the humeral head of the morbid humerus. To determine one of the connecting lines, computing system 702 may perform any one of various known algorithms for computing a geodesic path over a triangular mesh of points, such as the 3D model of the predicted premorbid humerus. For example, Surazhsky et al., "Fast Exact and Approximate Geodesics on Meshes," ACM Transactions on Graphics (TOG), Volume 24, Issue 3, July 2005, pages 553-560, describes an algorithm for determining a geodesic path over a triangular mesh of points. The white lines in FIG. 12C illustrate example connecting lines.

Furthermore, in the example of FIG. 11, computing system 702 may determine a geodesic surface that is defined by the connecting lines, the projected medial border of the Hill-Sachs lesion, and the projected medial border of the footprint of the humeral head of the morbid humerus (1112). For instance, in an example where the 3D model of the predicted premorbid humerus is defined by a mesh of triangles, computing system 702 may determine triangles or vertices of triangles of the 3D model of the predicted premorbid humerus that fall within the connecting lines, the projected medial border of the Hill-Sachs lesion, and the projected medial border of the footprint of the humeral head of the morbid humerus. As discussed above with respect to action (804), computing system 702 may determine an areal size of this geodesic surface and use that areal size to determine whether the bone loss involves joint engagement. Furthermore, as discussed elsewhere in this disclosure, computing system 702 may use the areal size of this geodesic surface to determine a minimum area of a bone graft.

Figure 13D:
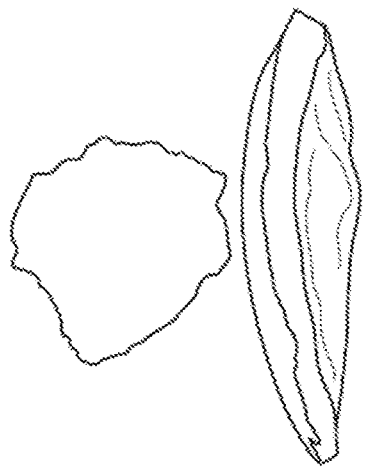
Figure 13E:
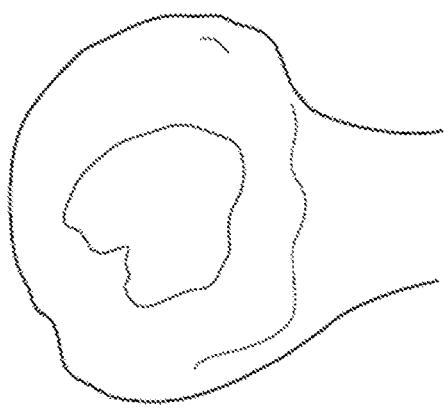
Figure 13F:
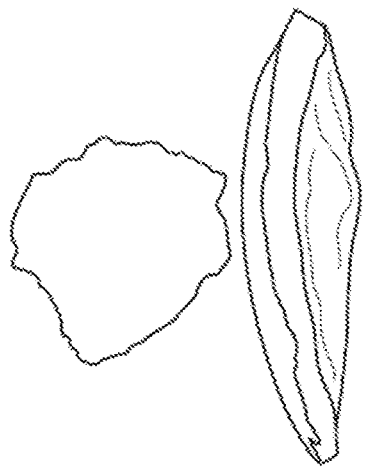

FIG. 13D is an example that shows a 3D model of the morbid humerus overlaying the 3D model of the predicted premorbid humerus. FIG. 13E is an example showing the geodesic surface that is defined by the connecting lines, the projected medial border of the Hill-Sachs lesion, and the projected medial border of the footprint of the humeral head of the morbid humerus overlaid on the 3D model of the morbid humerus. FIG. 13F is an example showing the geodesic surface and a 3-dimensional volume of the Hill-Sachs lesion.

Figure 14B:
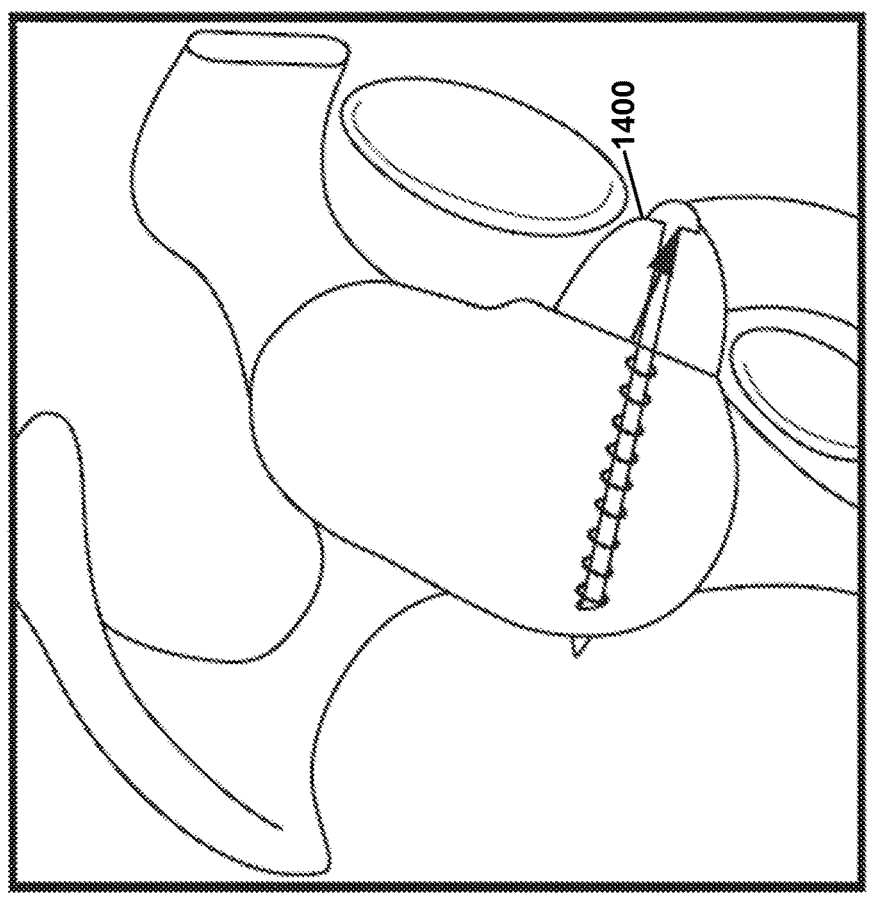
FIG. 14B is a conceptual diagram of bone grafting using a Bristow approach.
Figure 14A:
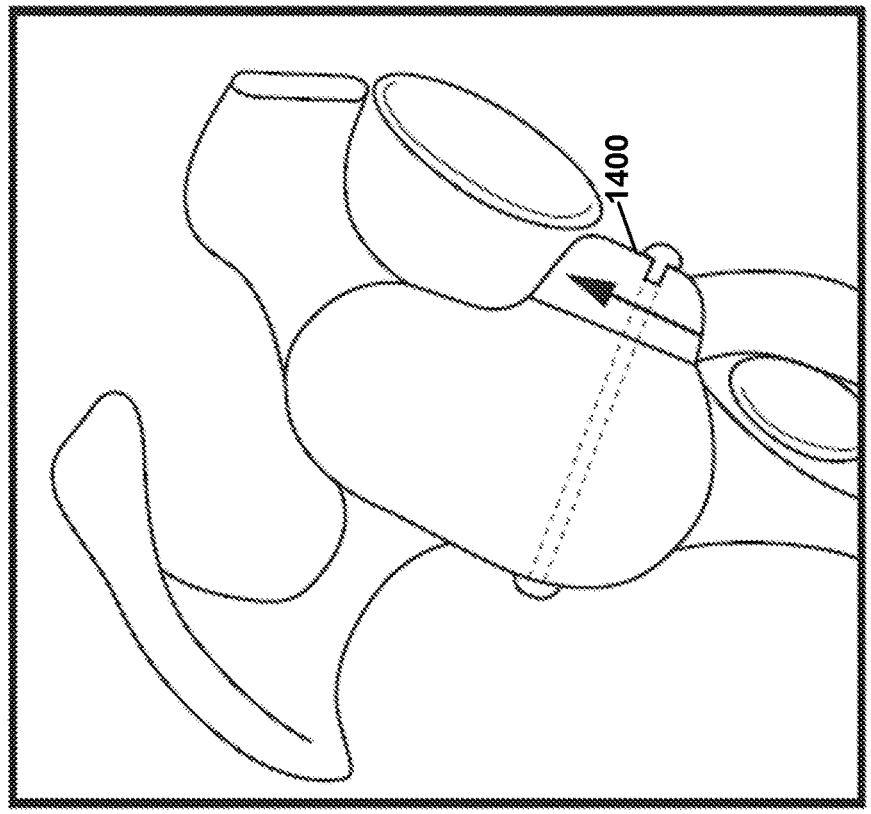
FIG. 14A is a conceptual diagram of bone grafting using a Latarjet approach.

In some examples where the patient's bone loss involves joint engagement, the surgeon may need to attach a bone graft to the anteroinferior border of the patient's glenoid bone. This may help keep the humeral head within the patient's glenoid cavity. Particularly, the surgeon may cut away a tip of the patient's coracoid process and reattach the tip of the patient's coracoid process to the anteroinferior border of the patient's glenoid bone. The Latarjet approach and the Bristow approach are two surgical approaches for attaching the severed tip of the coracoid process to the patient's glenoid bone. FIG. 14A is a conceptual diagram of bone grafting using a Latarjet approach. FIG. 14B is a conceptual diagram of bone grafting using a Bristow approach. As shown in the example of FIG. 14A, in the Latajet approach, the bone graft 1400 is attached to the glenoid bone with a vertical orientation. In other words, the long axis of bone graft 1400 may be generally aligned with a superior-inferior axis of the glenoid cavity. As shown in the example of FIG. 14B, in the Bristow approach, the bone graft 1400 is attached to the glenoid bone with a horizontal orientation. In other words, the long axis of bone graft 1400 may be generally aligned with the anterior-posterior axis of the glenoid cavity.

Figure 15:
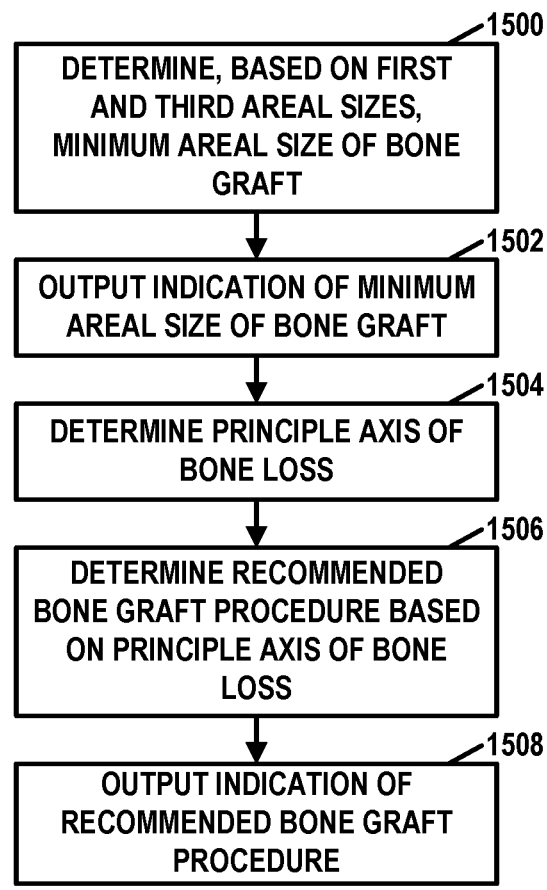
FIG. 15 is a flowchart illustrating an example operation that may be performed based on the computing system recommending a shoulder stability engagement surgery that includes a bone graft, in accordance with a technique of this disclosure.

FIG. 15 is a flowchart illustrating an example operation that may be based on computing system 702 recommending a shoulder stability engagement surgery that includes a bone graft, in accordance with a technique of this disclosure. Computing system 702 may perform the operation of FIG. 15 in response to determining (e.g., in action 806 of FIG. 8) that the bone loss involves joint engagement and, hence, may require the surgeon to perform a bone graft.

In the example of FIG. 15, computing system 14 may determine, based on the first areal size (i.e., the areal size of the predicted premorbid glenoid bone of the patient) and the third areal size (i.e., the areal size of a geodesic surface on the 3D model of the predicted premorbid humerus of the patient that is defined at least in part by the projected medial border of a Hill-Sachs lesion on the morbid humerus and the projected medial border of the footprint of the humeral head of the morbid humerus), a minimum areal size of a bone graft to be harvested from a coracoid process of the patient in a surgical procedure to attach the bone graft to the morbid glenoid bone (1500). The minimum areal size of the bone graft refers to a size of a 2-dimensional surface of the bone graft that is to be put into direct contact with the glenoid bone of the patient. In one example, computing system 14 may determine the minimum areal size of the bone graft as:

$$B_{min} = (0.83 \times A) - C$$

In the equation above, $B_{min}$ denotes the minimum areal size of the bone graft, "A" denotes the first areal size, and "C" denotes the third areal size. Thus, in this example, computing system 702 may determine the minimum areal size of the bone graft as a predetermined percentage value (e.g., an assumed percentage of the glenoid cavity covered by the humeral head during abduction and external rotation movement of the shoulder) multiplied by the first areal size, minus the third areal size.

In the example of FIG. 15, computing system 702 may output an indication of the minimum areal size of the bone graft (1502). For instance, computing system 702 may output an indication of the minimum areal size of the bone graft for display on a display screen, in a MR visualization, in a VR visualization, or in another manner. Knowing the minimum areal size of the bone graft may allow a surgeon to determine how much of the coracoid process to remove and how much area on the glenoid bone must be prepared.

Furthermore, in the example of FIG. 15, computing system 702 may determine a principal axis of bone loss on the glenoid bone of the patient (1504). In some examples, computing system 702 may use principal component analysis (PCA) to determine the principal axis of bone loss. That is, computing system 702 may generate a point cloud that comprises points that correspond to areas within the area of bone loss on the glenoid bone. Computing system 702 may then use a PCA algorithm to determine the principal axis of the bone loss.

Computing system 702 may then determine the recommended type of bone graft procedure based on the principal axis of bone loss (1506). In other words, computing system 702 may determine, based on the principal axis of bone loss on the glenoid bone, a recommended bone graft procedure for harvesting the bone graft from the coracoid process and attaching the bone graft to the morbid glenoid bone. For example, computing system 702 may compare the principal axis of bone loss to the infero-superior axis of the glenoid cavity. In some examples, computing system 702 may select the recommended bone graft procedure from among a Latarjet bone graft procedure and a Bristow bone graft procedure. In such examples, if the principal axis of the bone loss is aligned with the infero-superior axis, computing system 702 may recommend the Latarjet approach. If the principal axis of the bone loss is not more closely aligned with the infero-superior axis than the anterior-posterior axis of the glenoid cavity, computing system 702 may recommend the Bristow approach. In other examples, computing system 702 may select from three or more different types of bone graft procedures. In some examples, computing system 702 may indicate a volume or amount of bone that should be grafted onto the glenoid in order to correct the bone loss observed for the patient.

In the example of FIG. 15, computing system 702 outputs an indication of the recommended bone graft procedure (1508). For instance, computing system 702 may output an indication of the recommended bone graft procedure display on a display screen, in a MR visualization, in a VR visualization, or in another manner.

In some examples, computing system 702 may calculate an ISIS (e.g., a 3D ISIS) for the patient prior to performing the method of FIG. 15. In some such examples, computing system 702 may perform the method of FIG. 15 in response to determining that the 3D ISIS for the patient is greater than a particular threshold (e.g., 6). Thus, in some examples, computing system 702 may determine an ISIS for the patient. For instance, computing system 702 may determine a 3-D ISIS for the patient based on at least one of: a 3-dimensional shape or volume of the Hill-Sachs lesion, or a 3-dimensional shape or volume of the Bankart lesion. In the example of FIG. 15, computing system 702 may determine the first, second, and third areal sizes, and may determine whether bone loss of the patient involves joint engagement in response to determining that the ISIS is greater than a threshold (e.g., 3, 6, etc.).

In some examples, computing system 702 may simulate one or more types of movement of the humerus relative to the glenoid using 3D models of the humerus and glenoid. Such types of movement may include canonical types of movement such as abduction, adduction, external rotation, internal rotation, flexion, extension, horizontal adduction, and scapular plane abduction. For each of the one or more types of motion (or one or more combinations thereof), computing system 702 may determine whether there is a critical position, and if so, may determine a location of the critical position. For ease of explanation, this disclosure may refer to the canonical types of movements and combinations of the canonical types of movement (e.g., external rotation with abduction) as types of movement. The critical position for a type of movement is a position at which a dislocation (e.g., subluxation) of the humerus would occur if the movement were to continue. For example, a patient may experience subluxation of the patient's humerus if the patient raises their arm above 90° during abduction. Thus, in this example, the critical position for abduction in this patient occurs at 90°. In some examples, the critical position for a type of movement occurs when a Hill-Sachs lesion on the patient's humeral head is "on-track." In essence, a dislocation may occur when there is insufficient bone in either the humeral head or glenoid rim due to the presence of a Hill-Sachs lesion and/or Bankart lesion to retain the humeral head within the glenoid fossa when the patient performs a particular type of movement and the humeral head reaches the critical position relative to the glenoid bone.

In some examples, to determine the critical position for a type of movement, computing system 702 may determine a position of a Hill-Sachs lesion in a 3D model of the patient's humerus (e.g., a 3D model of the morbid humerus). For example, to determine the position of the Hill-Sachs lesion, computing system 702 may use statistical shape modeling (SSM) to generate a 3D SSM model of the patient's humerus (e.g., the 3D model of the predicted premorbid humerus). Computing system 702 may then compare the 3D model of the patient's humerus to the 3D SSM model of the patient's humerus. Computing system 702 may identify the Hill-Sachs lesion as a region of in which the 3D model of the patient's humerus is deflected inward toward the center of the humeral head relative to the 3D SSM model of the patient's humerus.

Additionally, as part of determining the critical position for the type of movement, computing system 702 may determine locations of bone loss on the patient's glenoid rim in a 3D model of the patient's glenoid bone (e.g., a 3D model of the morbid glenoid bone). For example, to determine the locations of bone loss on the patient's glenoid rim, computing system 702 may use SSM to generate a 3D SSM model of the patient's glenoid bone (e.g., a 3D model of the predicted premorbid glenoid bone). Computing system 702 may then compare the 3D model of the patient's glenoid bone to the 3D SSM model of the patient's glenoid bone. Computing system 702 may identify the locations of bone loss on the patient's glenoid rim as areas in which the 3D model of the patient's glenoid bone is deflected inward relative to the 3D SSM model of the patient's glenoid bone.

Furthermore, as part of determining the critical position for the type of movement, computing system 702 may register the 3D model of the patient's humerus with the 3D model of the patient's glenoid bone. In some examples, computing system 702 may use an iterative closest point (ICP) algorithm to register the 3D model of the patient's humerus with the 3D model of the patient's glenoid bone. Conceptually, registering the 3D model of the patient's humerus with the 3D model of the patient's glenoid bone positions the humeral head within the patient's glenoid fossa. After registration, computing system 702 may perform simulations to determine critical positions for one or more types of movements. Performing a simulation for a type of movement may involve moving the 3D model of the humerus in a manner consistent with the type of movement and determining an angle at which the critical position occurs. Computing system 702 may determine that the critical position occurs when at least a particular portion of the Hill-Sachs lesion is aligned with the locations of bone loss on the patient's glenoid rim.

In some examples, computing system 702 may use information about the critical position for a type of movement to determine how perform one or more aspects of a Bristow or Latarjet surgery. For example, computing system 702 may use information about the critical position for a type of movement to determine a shape (e.g., size, dimensions, and/or other spatial characteristics) of a bone fragment to sever from a donor bone of the patient, such as the patient's coracoid process or other bone (e.g., iliac bone, distal tibia, etc.). For instance, in one example, computing system 702 may determine a size of the bone fragment such that the bone fragment has a thickness of at least the sum of the inward deflection of the Bankart lesion and Hill-Sachs lesion relative to the 3D model of the predicted premorbid glenoid and the 3D model of the predicted premorbid humerus, respectively. In some examples, computing system 702 may determine one or more angles of an axis from a center of the graft to a distal tip of the graft relative to a bone surface to which the graft is to be attached. Computing system 702 may output this angle as an angle at which to cut the bone fragment from the donor bone.

In some examples, computing system 702 may use information about the critical position for a type of movement to determine a placement of the bone fragment on the glenoid bone. For instance, in one example, computing system 702 may modify the 3D model to include the bone fragment at a set of possible graft positions. Computing system 702 may then evaluate the critical positions for each of the possible graft positions (e.g., by virtually moving the model of the humerus relative to the model of the glenoid bone). Computing system 702 may select the graft position resulting in the greatest range of motion before the critical position is reached.

Thus, in some examples, computing system 702 may determine, based on the determination that the bone loss of the patient involves joint engagement, a critical position for a type of movement of the morbid humerus. Additionally, in such examples, computing system 702 may determine one or more of the following based on the critical position for the type of movement of the morbid humerus: a shape of the bone graft, or a placement of the bone graft on the glenoid bone.

In some examples, after determining a size of the bone graft and a placement of the bone graft on the glenoid bone, computing system 702 may determine a screw length and/or screw trajectory of a screw that will be used to attach the bone fragment to the glenoid bone at the determined location. For instance, in this example, computing system 702 may determine a density map for the glenoid bone. The density map may comprise 3D voxels corresponding to regions within the glenoid bone. A value of the voxel corresponds to a bone density of the corresponding region of the glenoid bone. The values may be in terms of Hounsfield units. Computing system 702 may use the density map to search for a target trajectory through the glenoid bone for securing the bone graft to the glenoid bone. The target trajectory may be the trajectory where a sum of values of regions intersected by the trajectory is greater than other trajectories and that does not come within specific safety distances from specific sensitive structures, such as nerves, cysts, blood vessels, etc. Computing system 702 may determine the screw length as a length of screw sufficient for attaching the bone graft to the glenoid bone along the target trajectory. For instance, computing system 702 may determine the screw length as one of a set of predetermined screw lengths that is a longest predetermined screw length that is shorter than a distance between an entry point of the target trajectory on the glenoid bone and an exit point of the target trajectory on the glenoid bone. Thus, computing system 702 may determine, based on the shape of the bone graft and/or placement of the bone graft on the glenoid bone, at least one of a screw length or screw trajectory of a screw to attach the bone graft to the glenoid bone.

Figure 16:
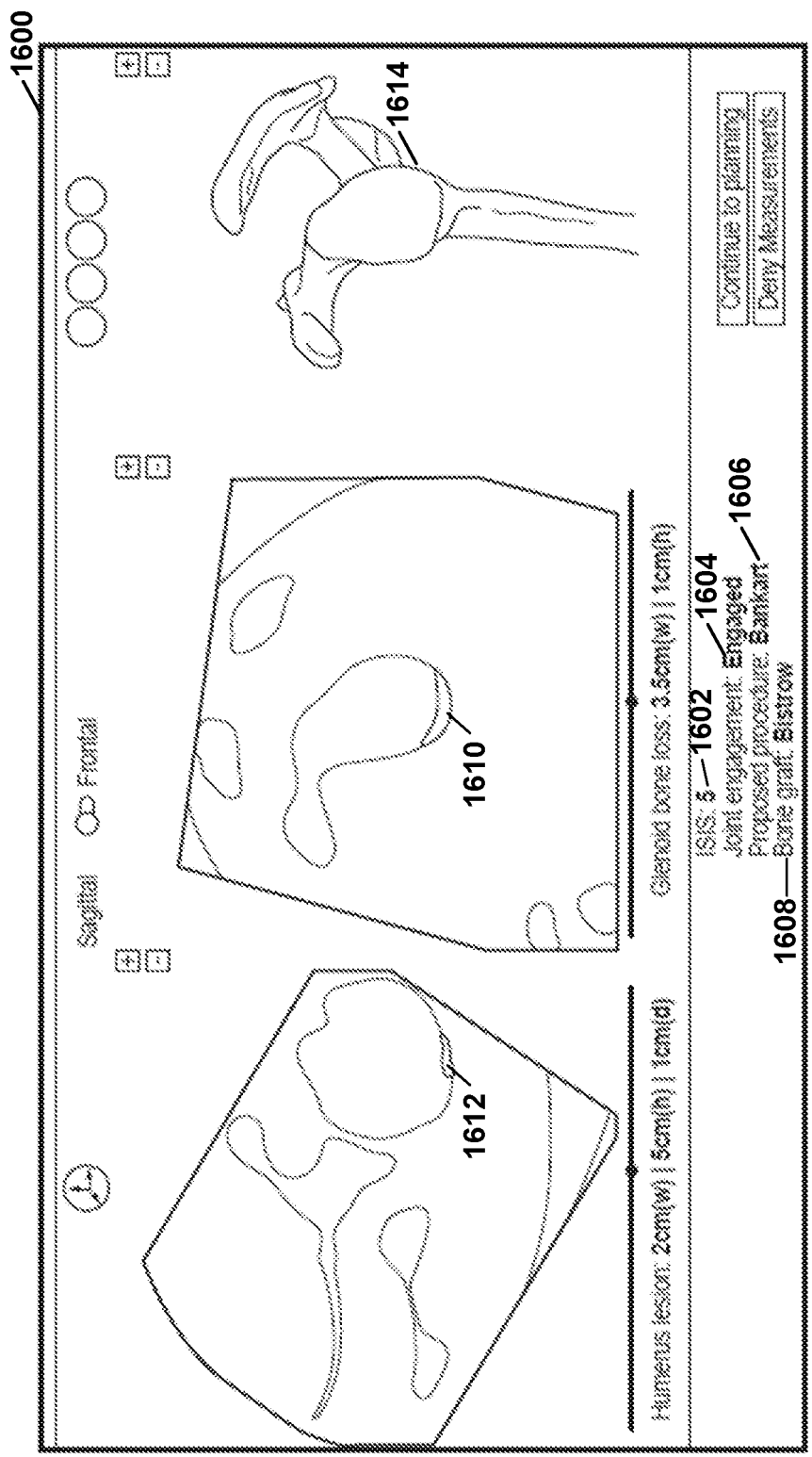
FIG. 16 is a conceptual diagram of an example user interface of surgical planning software, in accordance with one or more aspects of this disclosure.

FIG. 16 is a conceptual diagram of an example user interface 1600 of surgical planning software, in accordance with one or more aspects of this disclosure. Computing system 702 may output user interface 1600 for display, e.g., on a display screen, in a MR visualization, in a VR visualization, or in another manner.

As shown in the example of FIG. 16, user interface 1600 may indicate the ISIS for a patient 1602, an indication of whether the bone loss involves joint engagement 1604, a proposed surgical procedure 1606, and a proposed bone graft approach 1608. In the example of FIG. 16, user interface 1600 also indicates a Hill-Sachs lesion 1610 and a Bankart lesion 1612.

The rightmost part of user interface 1600 contains a 3D model 1614 of the glenoid bone and scapula of the patient. Although not shown in the example of FIG. 16, user interface 1600 may further include features indicating, with respect to 3D model 1614, a bone graft to be harvested from a coracoid process of the scapula. In some examples, user interface 1600 may include features indicating, with respect to 3D model 1614, a position and orientation of the bone graft with respect to the glenoid bone.

The following is a non-limiting set of examples that are in accordance with one or more techniques of this disclosure.

Example 1. A method comprising: determining, by a computing system, a first areal size as an areal size of a predicted premorbid glenoid bone of a patient; determining, by the computing system, a second areal size as an areal size of a Bankart lesion on a morbid glenoid bone of the patient; determining, by the computing system, a third areal size as an areal size of a geodesic surface on a 3-dimensional (3D) model of a predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein: the projected medial border of the Hill-Sachs lesion is a projection of a medial border of the Hill-Sachs lesion onto the 3D model of the predicted premorbid humerus, and the projected medial border of the footprint of the humeral head of the morbid humerus is a projection of a medial border of the footprint of the humeral head of the morbid humerus onto the 3D model of the predicted premorbid humerus; determining, by the computing system, based on the first, second, and third areal sizes, whether bone loss of the patient involves joint engagement; and based on a determination that the bone loss of the patient involves joint engagement, outputting, by the computing system, an indication that a shoulder stability enhancement surgery that includes a bone graft is recommended for the patient.

Example 2. The method of example 1, further comprising: based on the bone loss of the patient involving joint engagement, determining, based on the first areal size and the third areal size, a minimum areal size of the bone graft to be harvested from a coracoid process of the patient in a surgical procedure to attach the bone graft to the morbid glenoid bone; and outputting, by the computing system, an indication of the minimum areal size of the bone graft.

Example 3. The method of any of examples 1-2, further comprising: determining, by the computing system, a principal axis of bone loss on the morbid glenoid bone; determining, by the computing system, based on the principal axis of bone loss on the morbid glenoid bone, a recommended bone graft procedure for harvesting the bone graft from the coracoid process and attaching the bone graft to the morbid glenoid bone; and outputting, by the computing system, an indication of the recommended bone graft procedure.

Example 4. The method of example 3, wherein determining the recommended bone graft procedure comprises selecting, by the computing system, the recommended bone graft procedure from among a Latarjet bone graft procedure and a Bristow bone graft procedure.

Example 5. The method of any of examples 1-4, wherein: the method further comprises generating, by the computing system, based on one or more Computed Tomography (CT) scans of the patient, a 3D model of the morbid glenoid bone; and determining the second areal size comprises determining, by the computing system, based on a comparison of the 3D model of the morbid glenoid bone of the patient and a 3D model of the predicted premorbid glenoid bone, the areal size of the Bankart lesion on the morbid glenoid bone.

Example 6. The method of any of examples 1-5, wherein: the method further comprises generating, by the computing system, a 3D model of the morbid humerus; determining the third areal size comprises: determining, by the computing system, the medial border of the Hill-Sachs lesion on the 3D model of the morbid humerus; determining, by the computing system, the projected medial border of the Hill-Sachs lesion as the projection of the border of the Hill-Sachs lesion onto the 3D model of the predicted premorbid humerus; determining, by the computing system, the medial border of the footprint of the humeral head of the morbid humerus; determining, by the computing system, the projected medial border of the footprint of the humeral head of the morbid humerus as the projection of the medial border of the footprint of the humeral head of the morbid humerus onto the 3D model of the predicted premorbid humerus; and determining, by the computing system, connecting lines that connect the projected medial border of the Hill-Sachs lesion and the projected medial border of the footprint of the humeral head of the morbid humerus, the connecting lines being shortest geodesic paths over the 3D model of the predicted premorbid humerus from points on the projected medial border of the Hill-Sachs lesion to points on the projected medial border of the footprint of the humeral head of the morbid humerus, wherein the geodesic surface is defined by the connecting lines, the projected medial border of the Hill-Sachs lesion, and the projected medial border of the footprint of the humeral head of the morbid humerus.

Example 7. The method of example 6, wherein: the method further comprises outputting, by the computing system, the 3D model of the morbid humerus for display, and at least one of: (i) determining the medial border of the Hill-Sachs lesion on the 3D model of the morbid humerus comprises: receiving, by the computing system, indications of user input of first points along the medial border of the Hill-Sachs lesion on the 3D model of the morbid humerus; and interpolating, by the computing system, based on the first points, the medial border of the Hill-Sachs lesion on the 3D model of the morbid humerus, or (ii) determining the medial border of the footprint of the humeral head of the morbid humerus on the 3D model of the morbid humerus comprises: receiving, by the computing system, indications of user input of second points along the medial border of the footprint of the humeral head of the morbid humerus on the 3D model of the morbid humerus; and interpolating, by the computing system, based on the second points, the medial border of the footprint of the humeral head of the morbid humerus on the 3D model of the morbid humerus.

Example 8. The method of any of examples 1-7, wherein determining whether the bone loss of the patient involves joint engagement comprises: determining, by the computing system, an index value as a predetermined percentage value multiplied by the first areal size, minus the second areal size; and determining, by the computing system, whether the bone loss of the patient involves joint engagement based on whether the index value is greater than or less than the third areal value.

Example 9. The method of any of examples 1-8, wherein determining the minimum areal size of the bone graft comprises determining, by the computing system, the minimum areal size of the bone graft as a predetermined percentage value multiplied by the first areal size, minus the third areal size.

Example 10. The method of any of examples 1-9, wherein determining the areal size of the Bankart lesion comprises: determining, by the computing system, a projected premorbid glenoid surface as a projection of the predicted premorbid glenoid bone onto a glenoid plane; determining, by the computing system, a projected morbid glenoid surface as a projection of the morbid bone of the patient onto the glenoid plane; determining, by the computing system, based on the projected premorbid glenoid surface and the projected morbid glenoid surface, a zone of bone loss; and determining, by the computing system, the areal size of the Bankart lesion as an areal size of the zone of bone loss.

Example 11. The method of any of examples 1-10, wherein: the method further comprises determining an Instability Severity Index Score (ISIS) for the patient based on at least one of: a 3-dimensional shape or volume of the Hill-Sachs lesion, or a 3-dimensional shape or volume of the Bankart lesion, and the computing system determines the first, second, and third areal sizes, and determines whether bone loss of the patient involves joint engagement in response to determining that the ISIS is greater than a threshold.

Example 12. The method of any of examples 1-11, further comprising, based on the determination that the bone loss of the patient involves joint engagement: determining, by the computing system, a critical position for a type of movement of the morbid humerus; and determining, by the computing system, one or more of the following based on the critical position for the type of movement of the morbid humerus: a shape of the bone graft, or a placement of the bone graft on the glenoid bone.

Example 13. The method of example 12, further comprising determining, by the computing system, based on the shape of the bone graft and/or placement of the bone graft on the glenoid bone, at least one of a screw length or screw trajectory of a screw to attach the bone graft to the glenoid bone.

Example 14. A computing system comprising: a memory configured to store data describing a 3-dimensional (3D) model of a predicted premorbid humerus of a patient; and processing circuitry configured to: determine a first areal size as an areal size of a predicted premorbid glenoid bone of the patient of the patient; determine a second areal size as an areal size of a Bankart lesion on a morbid glenoid bone of the patient; determine a third areal size as an areal size of a geodesic surface on the 3D model of the predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein: the projected medial border of the Hill-Sachs lesion is a projection of a medial border of the Hill-Sachs lesion onto the 3D model of the predicted premorbid humerus, and the projected medial border of the footprint of the humeral head of the morbid humerus is a projection of a medial border of the footprint of the humeral head of the morbid humerus onto the 3D model of the predicted premorbid humerus; determine, based on the first, second, and third areal sizes, whether bone loss of the patient involves joint engagement; and based on a determination that the bone loss of the patient involves joint engagement, output an indication that a shoulder stability enhancement surgery that includes a bone graft is recommended for the patient.

Example 15. The computing system of example 14, wherein the processing circuitry is further configured to: based on the bone loss of the patient involving joint engagement, determine, based on the first areal size and the third areal size, a minimum areal size of the bone graft to be harvested from a coracoid process of the patient in a surgical procedure to attach the bone graft to the morbid glenoid bone; and output an indication of the minimum areal size of the bone graft.

Example 16. The computing system of any of examples 14-15, wherein the processing circuitry is further configured to: determine a principal axis of bone loss on the morbid glenoid bone; determine, based on the principal axis of bone loss on the morbid glenoid bone, a recommended bone graft procedure for harvesting the bone graft from the coracoid process and attaching the bone graft to the morbid glenoid bone; and output an indication of the recommended bone graft procedure.

Example 17. The computing system of example 16, wherein the processing circuitry is configured such that, as part of determining the recommended bone graft procedure, the processing circuitry selects the recommended bone graft procedure from among a Latarjet bone graft procedure and a Bristow bone graft procedure.

Example 18. The computing system of any of examples 14-17, wherein: the processing circuitry is further configured to generate, based on one or more Computed Tomography (CT) scans of the patient, a 3D model of the morbid glenoid bone, and the processing circuitry is configured such that, as part of determining the second areal size, the processing circuitry determines, based on a comparison of the 3D model of the morbid glenoid bone of the patient and a 3D model of the predicted premorbid glenoid bone, the areal size of the Bankart lesion on the morbid glenoid bone.

Example 19. The computing system of any of examples 14-18, wherein: the processing circuitry is further configured to generate a 3D model of the morbid humerus; the processing circuitry is configured such that, as part of determining the third areal size, the processing circuitry: determines the medial border of the Hill-Sachs lesion on the 3D model of the morbid humerus; determines the projected medial border of the Hill-Sachs lesion as the projection of the border of the Hill-Sachs lesion onto the 3D model of the predicted premorbid humerus; determines the medial border of the footprint of the humeral head of the morbid humerus; determines the projected medial border of the footprint of the humeral head of the morbid humerus as the projection of the medial border of the footprint of the humeral head of the morbid humerus onto the 3D model of the predicted premorbid humerus; and determines connecting lines that connect the projected medial border of the Hill-Sachs lesion and the projected medial border of the footprint of the humeral head of the morbid humerus, the connecting lines being shortest geodesic paths over the 3D model of the predicted premorbid humerus from points on the projected medial border of the Hill-Sachs lesion to points on the projected medial border of the footprint of the humeral head of the morbid humerus, wherein the geodesic surface is defined by the connecting lines, the projected medial border of the Hill-Sachs lesion, and the projected medial border of the footprint of the humeral head of the morbid humerus.

Example 20. The computing system of example 19, wherein: the processing circuitry is further configured to: output the 3D model of the morbid humerus for display, and at least one of: (i) the processing circuitry is configured such that, as part of determining the medial border of the Hill-Sachs lesion on the 3D model of the morbid humerus, the processing circuitry: receives the computing system, indications of user input of first points along the medial border of the Hill-Sachs lesion on the 3D model of the morbid humerus; and interpolates, based on the first points, the medial border of the Hill-Sachs lesion on the 3D model of the morbid humerus, or (ii) the processing circuitry is configured such that, as part of determining the medial border of the footprint of the humeral head of the morbid humerus on the 3D model of the morbid humerus, the processing circuitry: receives indications of user input of second points along the medial border of the footprint of the humeral head of the morbid humerus on the 3D model of the morbid humerus; and interpolates, based on the second points, the medial border of the footprint of the humeral head of the morbid humerus on the 3D model of the morbid humerus.

Example 21. The computing system of any of examples 14-20, wherein the processing circuitry is configured such that, as part of determining whether the bone loss of the patient involves joint engagement, the processing circuitry: determines an index value as a predetermined percentage value multiplied by the first areal size, minus the second areal size; and determines whether the bone loss of the patient involves joint engagement based on whether the index value is greater than or less than the third areal value.

Example 22. The computing system of any of examples 14-21, wherein the processing circuitry is configured such that, as part of determining the minimum areal size of the bone graft, the processing circuitry determines the minimum areal size of the bone graft as a predetermined percentage value multiplied by the first areal size, minus the third areal size.

Example 23. The computing system of any of examples 14-22, wherein the processing circuitry is configured such that, as part of determining the areal size of the Bankart lesion, the processing circuitry: determines a projected premorbid glenoid surface as a projection of the predicted premorbid glenoid bone onto a glenoid plane; determines a projected morbid glenoid surface as a projection of the morbid bone of the patient onto the glenoid plane; determines, based on the projected premorbid glenoid surface and the projected morbid glenoid surface, a zone of bone loss; and determines the areal size of the Bankart lesion as an areal size of the zone of bone loss.

Example 24. The computing system of any of examples 14-23, wherein: the processing circuitry is further configured to determine an Instability Severity Index Score (ISIS) for the patient based on at least one of: a 3-dimensional shape or volume of the Hill-Sachs lesion, or a 3-dimensional shape or volume of the Bankart lesion, and the processing circuitry is configured to determine the first, second, and third areal sizes, and determines whether bone loss of the patient involves joint engagement in response to determining that the ISIS is greater than a threshold.

Example 25. The computing system of any of examples 14-24, wherein the processing circuitry is further configured to, based on the determination that the bone loss of the patient involves joint engagement: determine a critical position for a type of movement of the morbid humerus; and determine one or more of the following based on the critical position for the type of movement of the morbid humerus: a shape of the bone graft, or a placement of the bone graft on the glenoid bone.

Example 26. The computing system of example 25, further comprising determining, by the computing system, based on the shape of the bone graft and/or placement of the bone graft on the glenoid bone, at least one of a screw length or screw trajectory of a screw to attach the bone graft to the glenoid bone.

Example 27. A computing system comprising: means for determining a first areal size as an areal size of a predicted premorbid glenoid bone of a patient; means for determining a second areal size as an areal size of a Bankart lesion on a morbid glenoid bone of the patient; means for determining a third areal size as an areal size of a geodesic surface on a 3-dimensional (3D) model of a predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein: the projected medial border of the Hill-Sachs lesion is a projection of a medial border of the Hill-Sachs lesion onto the 3D model of the predicted pre-morbid humerus, and the projected medial border of the footprint of the humeral head of the morbid humerus is a projection of a medial border of the footprint of the humeral head of the morbid humerus onto the 3D model of the predicted premorbid humerus; means for determining, based on the first, second, and third areal sizes, whether bone loss of the patient involves joint engagement; and means for outputting, based on a determination that the bone loss of the patient involves joint engagement, an indication that a shoulder stability enhancement surgery that includes a bone graft is recommended for the patient.

Example 28. The computing system of example 27, further comprising means for performing the methods of any of examples 2-13.

Example 29. A computer-readable data storage medium having instructions stored thereon that, when executed, cause a computing system to perform the methods of any of examples 1-13.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

What is claimed is:

1. A computing system comprising:
one or more memories configured to store data describing a 3-dimensional (3D) model of a predicted premorbid humerus of a patient; and
processing circuitry configured to:
determine a first areal size as an areal size of a predicted premorbid glenoid bone of the patient;
determine a second areal size as an areal size of a Bankart lesion on a morbid glenoid bone of the patient;
determine a third areal size as an areal size of a geodesic surface on the 3D model of the predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein:
the projected medial border of the Hill-Sachs lesion is a projection of a medial border of the Hill-Sachs lesion onto the 3D model of the predicted premorbid humerus, and
the projected medial border of the footprint of the humeral head of the morbid humerus is a projection of a medial border of the footprint of the humeral head of the morbid humerus onto the 3D model of the predicted premorbid humerus;
determine, based on the first, second, and third areal sizes, whether bone loss of the patient involves joint engagement; and
based on a determination that the bone loss of the patient involves joint engagement, output an indication that a shoulder stability enhancement surgery that includes a bone graft is recommended for the patient.

2. The computing system of claim 1, wherein the processing circuitry is further configured to:
based on the bone loss of the patient involving joint engagement, determine, based on the first areal size and the third areal size, a minimum areal size of the bone graft to be harvested from a coracoid process of the patient in a surgical procedure to attach the bone graft to the morbid glenoid bone; and
output an indication of the minimum areal size of the bone graft.

3. The computing system of claim 1, wherein the bone loss of the patient includes bone loss on the morbid glenoid bone and the processing circuitry is further configured to:
determine a principal axis of the bone loss on the morbid glenoid bone;
determine, based on the principal axis of the bone loss on the morbid glenoid bone, a recommended bone graft procedure for harvesting the bone graft from a coracoid process of the patient and attaching the bone graft to the morbid glenoid bone; and
output an indication of the recommended bone graft procedure.

4. The computing system of claim 3, wherein the processing circuitry is configured to, as part of determining the recommended bone graft procedure, select the recommended bone graft procedure from among a Latarjet bone graft procedure and a Bristow bone graft procedure.

5. The computing system of claim 1, wherein:
the processing circuitry is further configured to generate, based on one or more Computed Tomography (CT) scans of the patient, a 3D model of the morbid glenoid bone of the patient, and
the processing circuitry is configured to, as part of determining the second areal size, determine, based on a comparison of the 3D model of the morbid glenoid bone of the patient and a 3D model of the predicted premorbid glenoid bone, the areal size of the Bankart lesion on the morbid glenoid bone of the patient.

6. The computing system of claim 1, wherein:
the processing circuitry is further configured to generate a 3D model of the morbid humerus;
the processing circuitry is configured to, as part of determining the third areal size:
determine the medial border of the Hill-Sachs lesion on the 3D model of the morbid humerus;
determine the projected medial border of the Hill-Sachs lesion as the projection of the medial border of the Hill-Sachs lesion onto the 3D model of the predicted premorbid humerus;
determine the medial border of the footprint of the humeral head of the morbid humerus;
determine the projected medial border of the footprint of the humeral head of the morbid humerus as the projection of the medial border of the footprint of the humeral head of the morbid humerus onto the 3D model of the predicted premorbid humerus; and
determine connecting lines that connect the projected medial border of the Hill-Sachs lesion and the projected medial border of the footprint of the humeral head of the morbid humerus, the connecting lines being shortest geodesic paths over the 3D model of the predicted premorbid humerus from points on the projected medial border of the Hill-Sachs lesion to points on the projected medial border of the footprint of the humeral head of the morbid humerus,
wherein the geodesic surface is defined by the connecting lines, the projected medial border of the Hill-Sachs lesion, and the projected medial border of the footprint of the humeral head of the morbid humerus.

7. The computing system of claim 6, wherein:
the processing circuitry is further configured to:
output the 3D model of the morbid humerus for display, and at least one of:
(i) the processing circuitry is configured to, as part of determining the medial border of the Hill-Sachs lesion on the 3D model of the morbid humerus:
receive indications of user input of first points along the medial border of the Hill-Sachs lesion on the 3D model of the morbid humerus; and
interpolate, based on the first points, the medial border of the Hill-Sachs lesion on the 3D model of the morbid humerus, or
(ii) the processing circuitry is configured to, as part of determining the medial border of the footprint of the humeral head of the morbid humerus on the 3D model of the morbid humerus:
receive indications of user input of second points along the medial border of the footprint of the humeral head of the morbid humerus on the 3D model of the morbid humerus; and
interpolate, based on the second points, the medial border of the footprint of the humeral head of the morbid humerus on the 3D model of the morbid humerus.

8. The computing system of claim 1, wherein the processing circuitry is configured to, as part of determining whether the bone loss of the patient involves joint engagement:
determine an index value as a predetermined percentage value multiplied by the first areal size, minus the second areal size; and
determine whether the bone loss of the patient involves joint engagement based on whether the index value is greater than or less than the third areal size.

9. The computing system of claim 2, wherein the processing circuitry is configured to, as part of determining the minimum areal size of the bone graft, determine the minimum areal size of the bone graft as a predetermined percentage value multiplied by the first areal size, minus the third areal size.

10. The computing system of claim 1, wherein the processing circuitry is configured to, as part of determining the second areal size:
determine a projected premorbid glenoid surface as a projection of the predicted premorbid glenoid bone onto a glenoid plane;
determine a projected morbid glenoid surface as a projection of the morbid glenoid bone of the patient onto the glenoid plane;
determine, based on the projected premorbid glenoid surface and the projected morbid glenoid surface, a zone of bone loss; and
determine the areal size of the Bankart lesion as an areal size of the zone of bone loss.

11. The computing system of claim 1, wherein:
the processing circuitry is further configured to determine an Instability Severity Index Score (ISIS) for the patient based on at least one of:
a 3-dimensional shape or volume of the Hill-Sachs lesion, or
a 3-dimensional shape or volume of the Bankart lesion, and
the processing circuitry is configured to determine the first, second, and third areal sizes, and determine whether the bone loss of the patient involves joint engagement in response to determining that the ISIS is greater than a threshold.

12. The computing system of claim 1, wherein the processing circuitry is further configured to, based on the determination that the bone loss of the patient involves joint engagement:
determine a critical position for a type of movement of the morbid humerus; and
determine one or more of the following based on the critical position for the type of movement of the morbid humerus:
a shape of the bone graft, or
a placement of the bone graft on the morbid glenoid bone.

13. The computing system of claim 12, wherein the processing circuitry is further configured to determine, based on the shape of the bone graft and/or the placement of the bone graft on the glenoid bone, at least one of a screw length or screw trajectory of a screw to attach the bone graft to the glenoid bone.

14. A computing system comprising:
means for determining a first areal size as an areal size of a predicted premorbid glenoid bone of a patient;
means for determining a second areal size as an areal size of a Bankart lesion on a morbid glenoid bone of the patient;
means for determining a third areal size as an areal size of a geodesic surface on a 3-dimensional (3D) model of a predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein:
the projected medial border of the Hill-Sachs lesion is a projection of a medial border of the Hill-Sachs lesion onto the 3D model of the predicted premorbid humerus, and
the projected medial border of the footprint of the humeral head of the morbid humerus is a projection of a medial border of the footprint of the humeral head of the morbid humerus onto the 3D model of the predicted premorbid humerus;
means for determining, based on the first, second, and third areal sizes, whether bone loss of the patient involves joint engagement; and
means for outputting, based on a determination that the bone loss of the patient involves joint engagement, an indication that a shoulder stability enhancement surgery that includes a bone graft is recommended for the patient.

15. A method comprising:
storing data describing a 3-dimensional (3D) model of a predicted premorbid humerus of a patient;
determining, by one or more processors, a first areal size as an areal size of a predicted premorbid glenoid bone of the patient;
determining, by the one or more processors, a second areal size as an areal size of a Bankart lesion on a morbid glenoid bone of the patient;
determining, by the one or more processors, a third areal size as an areal size of a geodesic surface on the 3D model of the predicted premorbid humerus of the patient, wherein the geodesic surface is defined at least in part by (i) a projected medial border of a Hill-Sachs lesion on a morbid humerus and (ii) a projected medial border of a footprint of a humeral head of the morbid humerus, wherein:
the projected medial border of the Hill-Sachs lesion is a projection of a medial border of the Hill-Sachs lesion onto the 3D model of the predicted premorbid humerus, and
the projected medial border of the footprint of the humeral head of the morbid humerus is a projection of a medial border of the footprint of the humeral head of the morbid humerus onto the 3D model of the predicted premorbid humerus;
determining, by the one or more processors, based on the first, second, and third areal sizes, whether bone loss of the patient involves joint engagement; and
based on a determination that the bone loss of the patient involves joint engagement, outputting, by the one or more processors, an indication that a shoulder stability enhancement surgery that includes a bone graft is recommended for the patient.

16. The method of claim 15, further comprising:
based on the bone loss of the patient involving joint engagement, determining, by the one or more processors, based on the first areal size and the third areal size, a minimum areal size of the bone graft to be harvested from a coracoid process of the patient in a surgical procedure to attach the bone graft to the morbid glenoid bone; and outputting, by the one or more processors, an indication of the minimum areal size of the bone graft.

17. The method of claim 15, wherein the bone loss of the patient includes bone loss on the morbid glenoid bone and the method further comprises:
determining, by the one or more processors, a principal axis of the bone loss on the morbid glenoid bone;
determining, by the one or more processors, based on the principal axis of the bone loss on the morbid glenoid bone, a recommended bone graft procedure for harvesting the bone graft from a coracoid process of the patient and attaching the bone graft to the morbid glenoid bone; and
outputting, by the one or more processors, an indication of the recommended bone graft procedure.

18. The method of claim 15, wherein:
the method further comprises generating, by the one or more processors, based on one or more Computed Tomography (CT) scans of the patient, a 3D model of the morbid glenoid bone, and
determining the second areal size comprises determining, by the one or more processors, based on a comparison of the 3D model of the morbid glenoid bone of the patient and a 3D model of the predicted premorbid glenoid bone, the areal size of the Bankart lesion on the morbid glenoid bone.

19. The method of claim 15, wherein:
the method further comprises generating, by the one or more processors, a 3D model of the morbid humerus;
determining the third areal size comprises:
determining the medial border of the Hill-Sachs lesion on the 3D model of the morbid humerus;
determining the projected medial border of the Hill-Sachs lesion as the projection of the medial border of the Hill-Sachs lesion onto the 3D model of the predicted premorbid humerus;
determining the medial border of the footprint of the humeral head of the morbid humerus;
determining the projected medial border of the footprint of the humeral head of the morbid humerus as the projection of the medial border of the footprint of the humeral head of the morbid humerus onto the 3D model of the predicted premorbid humerus; and
determining connecting lines that connect the projected medial border of the Hill-Sachs lesion and the projected medial border of the footprint of the humeral head of the morbid humerus, the connecting lines being shortest geodesic paths over the 3D model of the predicted premorbid humerus from points on the projected medial border of the Hill-Sachs lesion to points on the projected medial border of the footprint of the humeral head of the morbid humerus,
wherein the geodesic surface is defined by the connecting lines, the projected medial border of the Hill-Sachs lesion, and the projected medial border of the footprint of the humeral head of the morbid humerus.

20. The method of claim 19, wherein:
the method further comprises outputting, by the one or more processors, the 3D model of the morbid humerus for display, and
at least one of:
(i) determining the medial border of the Hill-Sachs lesion on the 3D model of the morbid humerus comprises:
receiving indications of user input of first points along the medial border of the Hill-Sachs lesion on the 3D model of the morbid humerus; and
interpolating, based on the first points, the medial border of the Hill-Sachs lesion on the 3D model of the morbid humerus, or
(ii) determining the medial border of the footprint of the humeral head of the morbid humerus on the 3D model of the morbid humerus comprises:
receiving indications of user input of second points along the medial border of the footprint of the humeral head of the morbid humerus on the 3D model of the morbid humerus; and
interpolating, based on the second points, the medial border of the footprint of the humeral head of the morbid humerus on the 3D model of the morbid humerus.

* * * * *